(12) United States Patent
Hayashi et al.

(10) Patent No.: US 6,257,721 B1
(45) Date of Patent: Jul. 10, 2001

(54) DEVICE FOR SPECTACLES

(75) Inventors: Akihiro Hayashi; Yoshinobu Hosoi, both of Aichi (JP)

(73) Assignee: Nidek Co., Ltd., Aichi (JP)

( * ) Notice: Subject to any disclaimer, the term of this patent is extended or adjusted under 35 U.S.C. 154(b) by 0 days.

(21) Appl. No.: 09/507,671

(22) Filed: Feb. 22, 2000

(30) Foreign Application Priority Data

Feb. 22, 1999 (JP) .................................. 11-043965
Apr. 9, 1999 (JP) .................................. 11-103309

(51) Int. Cl.$^7$ ...................................................... A61B 3/10
(52) U.S. Cl. ............................................................ 351/204
(58) Field of Search ................................... 351/200, 204, 351/205, 245, 246

(56) References Cited

U.S. PATENT DOCUMENTS

| 4,591,246 | 5/1986 | Cousyn et al. . |
|---|---|---|
| 4,845,641 | 7/1989 | Ninomiya et al. . |
| 4,944,585 | 7/1990 | Mizuno . |
| 5,617,155 | 4/1997 | Ducarouge et al. . |
| 5,640,219 | 6/1997 | Ramachandran . |
| 5,691,799 | * 11/1997 | Ramachandran ..................... 351/204 |
| 5,764,341 | 6/1998 | Fujieda et al. . |

FOREIGN PATENT DOCUMENTS

| 6-63015 | 3/1994 | (JP) | .................. A61B/3/04 |
|---|---|---|---|
| 8-98810 | 4/1996 | (JP) | .................. A61B/3/11 |
| 9-90297 | 4/1997 | (JP) | ................. G02C/13/00 |
| 9-145324 | 6/1997 | (JP) | ................. G01B/11/00 |

* cited by examiner

Primary Examiner—George Manuel
(74) Attorney, Agent, or Firm—Sughrue, Mion, Zinn & Macpeak & Seas, PLLC

(57) ABSTRACT

In a device for spectacles for measuring eye points of a subject, an index is presented to the subject, a positional relationship between an eye of the subject and the index is varied, and the eye points of the subject is measured based on information about the positional relationship between the subject's eye and the index.

22 Claims, 16 Drawing Sheets

FIG.14A
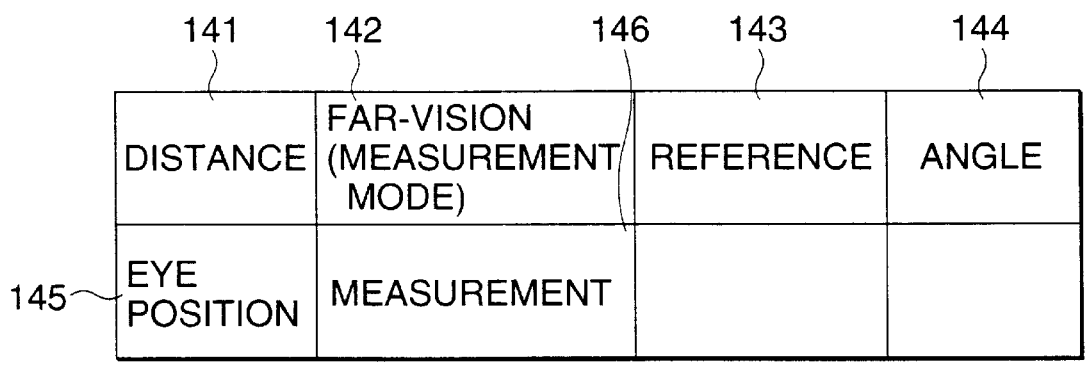
| DISTANCE | FAR-VISION (MEASUREMENT MODE) | REFERENCE | ANGLE |
|---|---|---|---|
| EYE POSITION | MEASUREMENT | | |
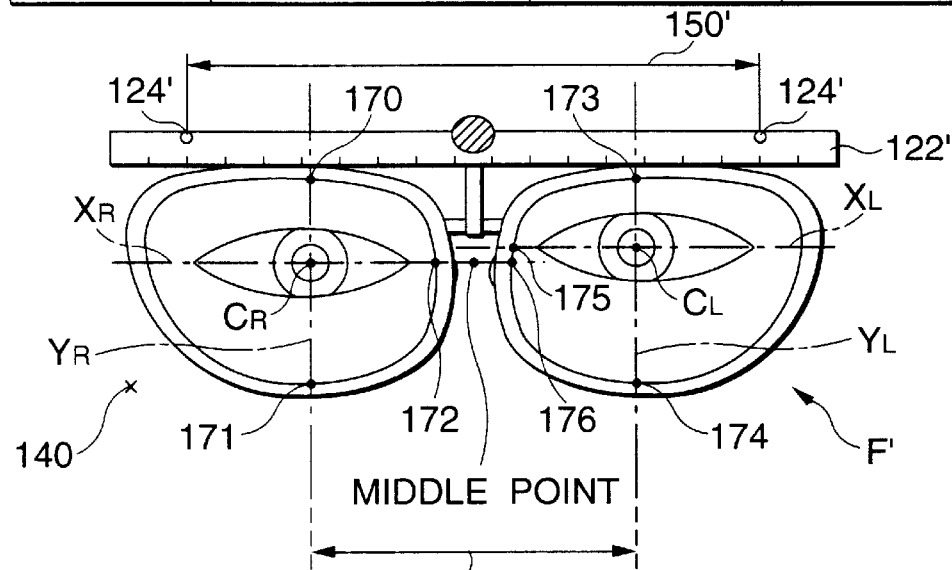
FIG.14B
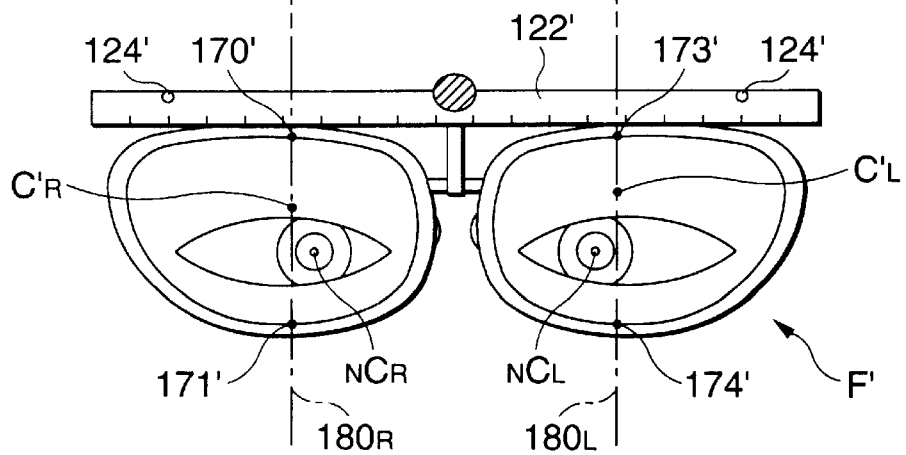

DEVICE FOR SPECTACLES

BACKGROUND OF THE INVENTION

1. Field of the Invention

The present invention relates to a device for spectacles for measuring eye points of a subject with respect to a spectacle frame.

2. Description of Related Art

In adjusting spectacles, it is important to measure eye points, such as the sighting position (visual line position) of a customer (hereinafter referred to as a subject) with respect to a spectacle frame selected by the subject and the pupillary distance.

Conventionally, for the measurement of the eye points, methods such as a method of marking the sighting position (visual line position) of the subject on spectacle lenses with a marker pen by the inspector with the subject sighting horizontally, and a method of attaching an eye point marking sticker at the position of the sight by confirming the near sighting position (visual line position) and the position of the pupils at a short distance (so-called mirror method) have been executed.

Moreover, for obtaining the inter-pupillary center distance (hereinafter referred to as PD),a pupillary distance measuring device has been used (see U.S. Pat. No. 4,944,585). Further, the PD has been measured by an eye refractive power measuring apparatus for automatically measuring the refractive power of an eye (see U.S. Pat. No 5,764,341).

Furthermore, an apparatus for photographing the face of a subject with a spectacle frame on by a television camera for finding the eye points by the photographed image (see JP-A-9-145324) has been proposed.

However, since the method of marking with a marker pen and the method of attaching a sticker executed according to observation of the sighting state of the subject by the inspector, it is highly dependent on the positional relationship between the subject and the inspector, and the experience of the inspector, and thus it is liable to be inaccurate. Moreover, these methods requires much time in measurement.

Further, since the PD obtained by the pupillary distance measuring device or the eye refractive power measuring apparatus is utilized for adjusting spectacles without examining the position with respect to the spectacle frame, it is liable that the pupillary center and the optical center of the produced spectacles do not coincide. Moreover, although the pupillary distance measuring device is fixed to the face of the subject by a nose contact member, since the nose shapes of subjects vary, an error can easily be generated depending on the contacting state.

Furthermore, the apparatus for finding the eye points from the photographed image by the television camera requires a complicated apparatus configuration, and thus a problem of a high cost is involved. Moreover, since the apparatus is the objective type, it is disadvantageous in that whether or not the measured position is correct cannot be confirmed by the subject himself. Further, according to the apparatus, since the face of the subject is photographed by the television camera in a fixed state, the measured eye position can be inaccurate depending on the difference of the targeted distance of sight in use by the subjects.

Furthermore, recently, progressive (progressive multifocus) lenses have been demanded increasingly. In the case of a progressive lens, positioning with respect to the eyes is particularly important compared with the case of a single focus lens. That is, it is necessary to measure the eye points for the far vision and the near vision further accurately for a progressive lens, depending on the subject's environment of use. However, the eye points for the far vision and the near vision in a progressive lens cannot be measured accurately according to conventional methods and apparatus. Moreover, the subject cannot learn easily how the optical pattern distribution of the progressive lenses with different styles provided by different manufacturers can influence his vision in relation to the position of the eye points.

SUMMARY OF THE INVENTION

In view of the prior art, an object of the invention is to provide a device for measuring the subjective eye points of the subject himself quickly with a simple configuration.

Moreover, another object of the invention is to provide a device for measuring the eye points of the subject accurately in the state according to the environment of use of the subject.

The present invention provides the followings:

1) A device for spectacles for measuring eye points of a subject, comprising:

presenting means for presenting an index to the subject;

varying means for varying a positional relationship between an eye of the subject and the index; and measuring means for measuring the eye points of the subject based on information about the positional relationship between the subject's eye and the index.

2) The device for spectacles according to 1), wherein the presenting means comprises:

a transmission type display disposed adjacent to a spectacular frame of a spectacles worn by the subject; and display control means for showing on the display a graphic pattern for measuring an eye point each corresponding to the left eye and the right eye as the index, with the graphic pattern provided such that the subject can judge whether or not the positional relationship between the graphic pattern and the sight of the subject directed to a chart is appropriate, the varying means comprises:

moving means for moving the graphic pattern so as to dispose the graphic pattern and the subject's sight with a predetermined positional relationship, the measuring means comprises:

detecting means for detecting a moving amount by the moving means; and determining means for determining the eye point of the subject based on the detected moving amount.

3) The device for spectacles according to 2), further comprising mounting means for mounting the display on the spectacular frame front surface of the spectacles worn by the subject.

4) The device for spectacles according to 2), wherein the graphic pattern comprises a small spot-like light transmission region, with the light transmission region provided with a larger light transmission amount compared with a peripheral region thereof.

5) The device for spectacles according to 2), wherein the moving means comprises means operable by the subject himself, and the device for spectacles further comprising voice guide means for generating a voice guide for guiding the operation by the subject in measuring the eye point.

6) The device for spectacles according to 2), wherein the display control means further shows on the display a second graphic pattern for measuring a position of an inner periphery of the spectacular frame.

7) The device for spectacles according to 6), wherein the second graphic pattern comprises a longitudinal line and a lateral line.

8) The device for spectacles according to 1), wherein the presenting means comprises:
   a transmission type display disposed adjacent to a spectacular frame of a spectacles worn by the subject; and
   first display control means for showing on the display a graphic pattern for measuring an eye point each corresponding to the left eye and the right eye as the index,
   the varying means comprises:
      moving means for moving the graphic pattern so as to dispose the graphic pattern and the subject's sight with a predetermined positional relationship,
   the measuring means comprises:
      detecting means for detecting a moving amount by the moving means, and
      determining means for determining the eye point of the subject based on the detected moving amount,
   the device for spectacles further comprising:
   memory means for storing a distribution pattern of a far-vision region, a progressive region, and a near-vision region in a progressive lens, and
   second display control means for displaying the distribution pattern on the display.

9) The device for spectacles according to 8), wherein the second display control means determines a display position of the distribution pattern based on at least one of the detection result by the position detecting means and the determination result by the determining means.

10) The device for spectacles according to 8), wherein the memory means stores a plurality of distribution patterns, and
   the device for spectacles further comprising selecting means for selecting one from the stored plurality of the distribution patterns.

11) The device for spectacles according to 1), wherein the presenting means comprises:
   a gazing target presenting optical system comprising a gazing target to be gazed at by subject's eyes,
   the device for spectacles further comprising:
   a photographing optical system comprising photographing means for photographing a front eye part including both eyes of the subject,
   wherein the varying means varies the presenting distance of the gazing target optically, the varying means further varies the photographing distance by the photographing means optically for photographing from the substantially same position with respect to the gazing target, and the measuring means measures the eye points of the subject based on the image photographed by the photographing means and the positional relationship between the subject's eyes and at least one of the gazing target and the photographing means.

12) The device for spectacles according to 11), wherein the photographing optical system comprises the same optical path with the gazing target presenting optical system, and an optical member on the common optical path,
   the varying means moves the optical member for varying the presenting distance of the gazing target and the photographing distance by the photographing means optically.

13) The device for spectacles according to 11), wherein the photographing means can be detached from the photographing optical system so as to be disposed at a gazing position with a near-vision distance desired by the subject for photographing the front eye part of the subject.

14) The device for spectacles according to 11), further comprising:
   distance detecting means for detecting a distance between the subject and at least one of the gazing target and the photographing means, and
   advice means for advising the detected distance information,
   wherein the presenting distance of the gazing target can be varied by the varying means to the targeted distance of use of the spectacles desired by the subject based on the advised distance information.

15) The device for spectacles according to 11), wherein the measuring means comprises means for finding out at least one selected form the group consisting of an inter-pupillary center distance of the both eyes and the eye points with respect to a spectacular frame of a spectacles worn by the subject.

16) The device for spectacles according to 11), further comprising tilt angle detecting means for detecting a tilt angle of the photographing means in a photographing direction with respect to a horizontal direction.

17) The device for spectacles according to 11), wherein the gazing target presenting optical system and the photographing optical system are accommodated in a handy type housing.

18) The device for spectacles according to 11), further comprising distance detecting means for detecting the distance between the subject and at least one of the gazing target and the photographing means,
   wherein the measuring means measures the eye points of the subject based on the image photographed by the photographing means and the detected distance.

The present disclosure relates to the subject matter contained in Japanese patent application Nos. Hei. 11-43965 (filed on Feb. 22, 1999) and Hei. 11-103309 (filed on Apr. 9, 1999), which are expressly incorporated herein by reference in their entireties.

BRIEF DESCRIPTION OF THE DRAWINGS

FIGS. 14A and 14B are diagrams for explaining the method for finding the eye points and the PD from the image data shown on the display.

DESCRIPTION OF THE PREFERRED EMBODIMENT

<Embodiment 1>

Figure 1:
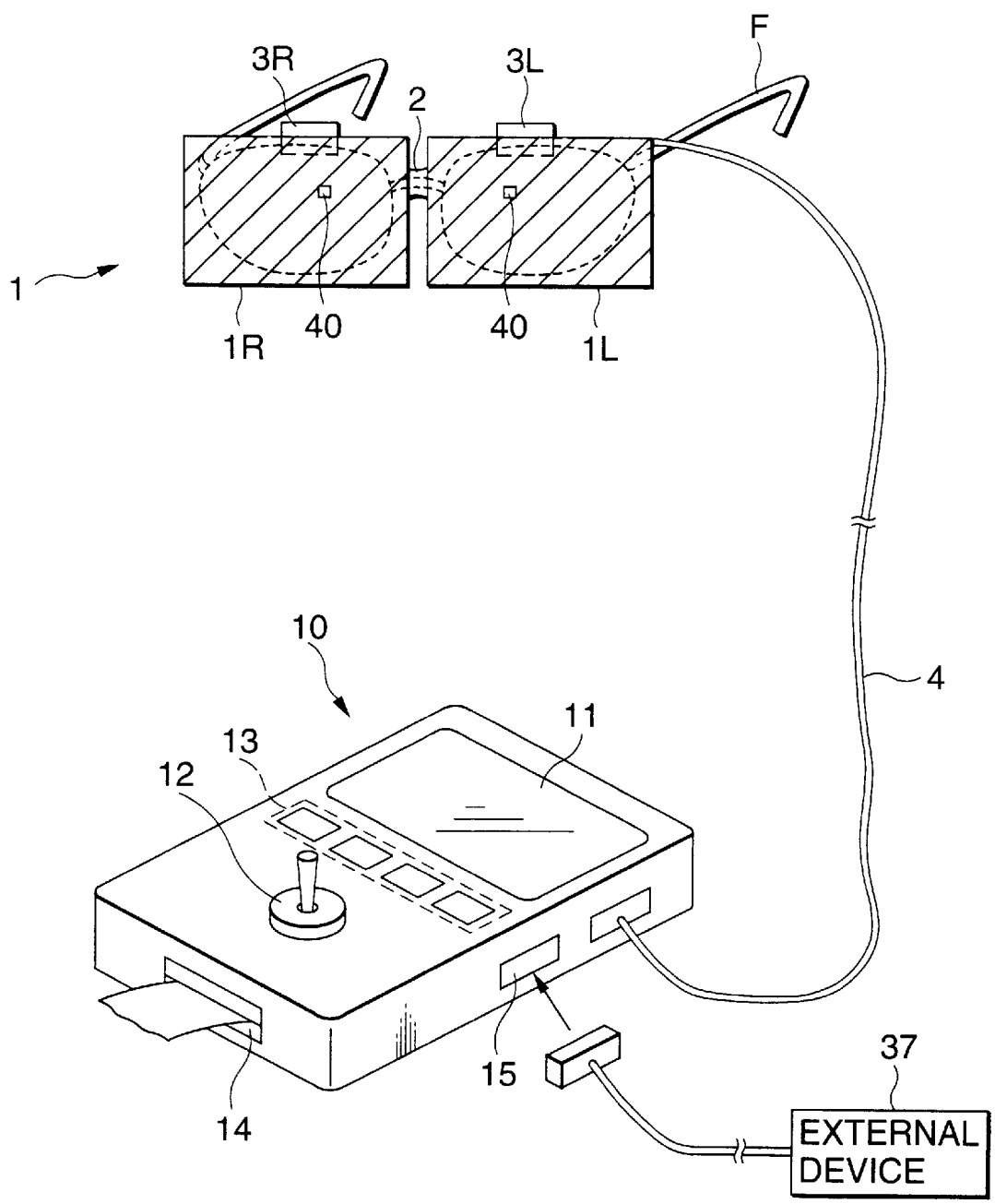
FIG. 1 is a diagram showing the external appearance of a device according to a first embodiment of the invention.
Figure 2:
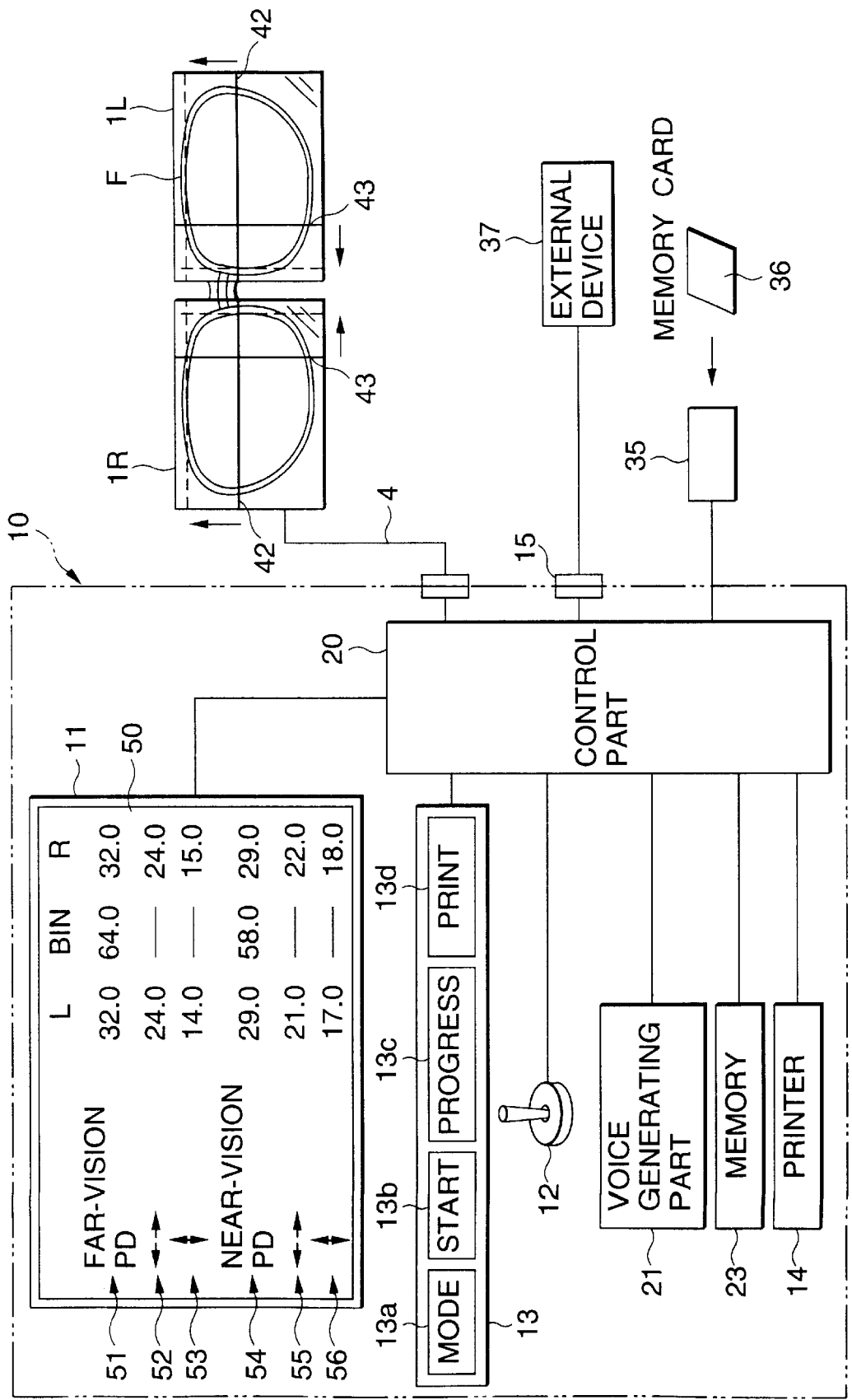
FIG. 2 is a chart showing the configuration of the control system of the device according to the first embodiment.

Hereinafter an embodiment of the invention will be explained with reference to the drawings. FIG. 1 is diagram showing the external appearance of a device according to the invention. FIG. 2 is a chart showing the configuration of the control system.

Numeral 1 is a liquid crystal panel part to be mounted on the front side of an spectacle frame F to be worn by a subject. The panel part 1 comprises transmission type liquid crystal displays 1R, 1L of a matrix system, to be disposed at the right and left side of the frame F. The displays 1R, 1L, which are jointed integrally by a joint member 2, can be mounted detachably to the front side of the frame F by mounting members 3R, 3L comprising a clip. The displays can indicate the transmission state or the light blocking state freely by the matrix system, however, since the configuration or the control itself is not characteristic of the invention and a known technique can be used, explanation thereof is not given here.

Numeral 10 is a control part connected with the panel part 1 by a communication cable 4. In the front panel of the control part 10 are disposed a display part 11 for indicating the measurement result and the information for selecting a progressive lens type (described later), a lever 12 for moving a pattern for positioning displayed on the panel part 1, and a switch part 13 comprising various kinds of switches for dispatching a command to the device (control part 20). In the switch part 13 are disposed a mode switch 13a for switching the mode for executing the eye point measurement and the progressive lens simulation, a start switch 13b for starting a measuring program of the eye point measuring mode, a progress switch 13c for proceeding the measuring program, and a print switch 13d (see FIG. 2). Numeral 14 is a printer for printing and outputting the measurement result, and 15 is a connector for connecting a cable for data transfer to another external device 37.

In FIG. 2, numeral 20 is a control part of the device, which has a program for measuring the eye points. Numeral 21 is a voice generating part for providing a command by a voice guide in executing the program for measuring the eye points, and 23 is a rewritable memory for storing data of a progressive lens to be used in the progressive lens simulation.

Eye point measurement according to the device will be explained. With a subject wearing a frame F he has chosen, an inspector fixes the panel part 1 on the front side of the frame F by the mounting members 3R, 3L after adjusting the wearing state. Moreover, the eye point measuring mode is set by the mode switch 13a. After the preparation, according to press of the start switch 13b by the subject himself, the measuring program is executed by the control part 20. The eye point measurement can be executed by operation of the lever 12 and the switches in the control part 10 according to the voice guide by the voice generating part 21 controlled by the control part 20 with the subject himself capable of confirming the viewing condition.

Figure 3:
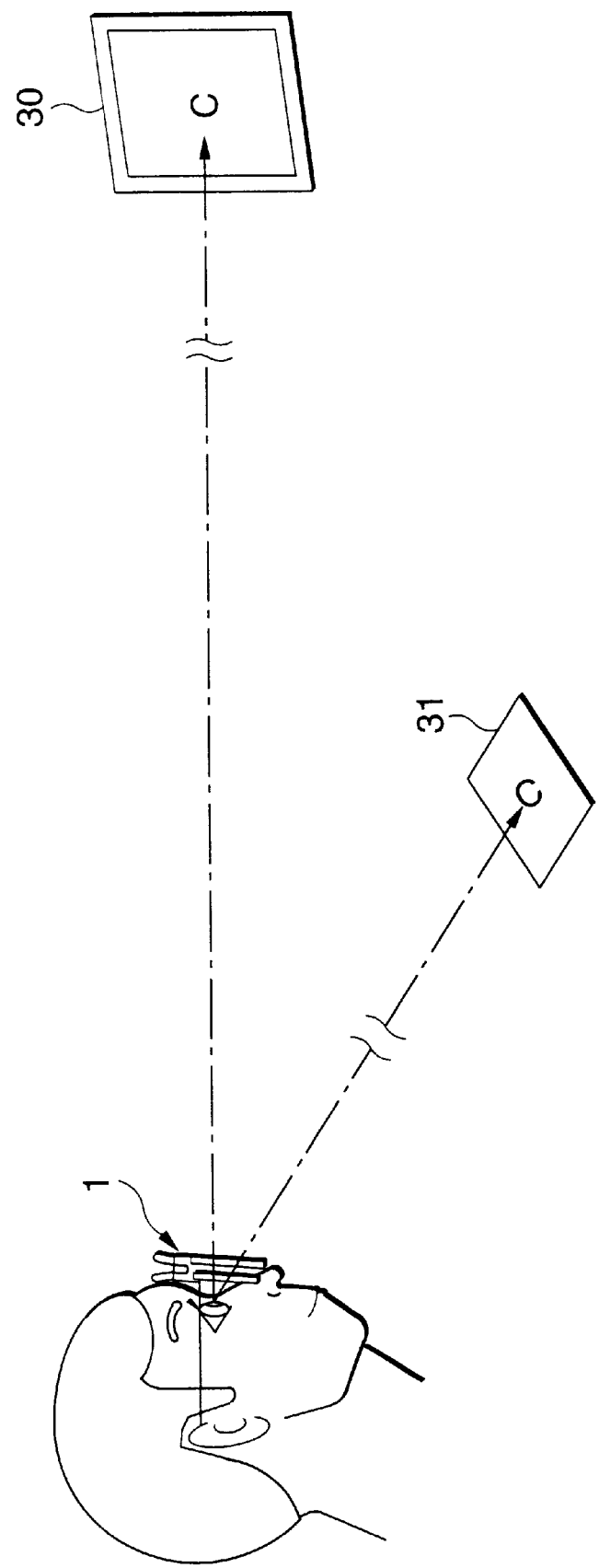
FIG. 3 is a diagram showing the state of a subject observing a chart in measuring the eye points for the far vision and the eye points for the near vision.

When the start switch 13b is turned on, a light transmission hole 40 pattern having a transmission region of about 3 mm square as an index is displayed on the display 1R by the liquid crystal pattern (see FIG. 1). That is, the periphery thereof is provided as the light blocking part by the liquid crystal pattern so as to provide the light transmission hole 40. At the same time, a voice command that "Adjust the hole in front of the eye so as to coincide with the center of the distant chart by tilting the lever, and press the progress button" is given from the voice generating part 21. As shown in FIG. 3, a far-vision chart to be projected by a chart projector 30 is disposed preliminarily in the horizontally forward direction from the subject (the chart projector 30 can either project a chart actually at a predetermined far distance, such as 5 m, or provide a chart optically at a far distance by a concave mirror disposed in a housing).

The signal of the lever 12 operated by the subject is inputted to the control part 20 so that the control part 20 controls the display on the display 1R so as to move the light transmission hole 40 in the vertical and horizontal directions according to the signal input. According to the movement of the light transmission hole 40 for disposing the chart at the far vision coinciding with the center of the light transmission hole 40 by the subject, the central coordinates of the light transmission hole 40 is determined as the viewing position (visual line position) of the right eye. When the progress switch 13c is pressed, similarly, the light transmission hole 40 is displayed on the display 1L as well as the command of the voice guide is given from the voice generating part 21. Similar to the case of the right eye side, the subject moves the light transmission hole 40 according to operation of the lever 12 so as to determine the viewing position (visual line position) for the far vision of the left eye side.

The light transmission hole 40 on the displays 1R, 1L can be provided in any form as long as the center of the light transmission hole 40 can be provided as the guide of the viewing position (visual line position) when the subject views the chart therethrough (any pattern having a transmission region with a visible pattern can be used), in addition to the method of having the entire region except the light transmission hole 40 in the light blocking state, a method of marking only the region surrounding the light transmission hole 40 so as to be partially in the light blocking state, or a method of facilitating recognition of the moving direction of the light transmission hole 40 with respect to the chart by providing the light transmission part in a half-transmittable state without completely blocking the light, can also be used.

When the progress switch 13c is pressed after the determination of the viewing positions (eye points) for the far vision, the eye point measurement is executed for the near vision. As shown in FIG. 3, a near-vision chart 31 is preliminarily disposed on a table in front of the subject at a desired short distance. A voice command that "Adjust the hole in front of the eye so as to coincide with the center of the near chart by tilting the lever, and press the progress button" is given from the voice generating part 21. Similar to the case of the far-vision, the subject moves the light transmission hole 40 at the display 1R side by the lever 12 so as to coincide with the desired near-vision sighting position (visual line position). After pressing the progress switch 13c, in the same manner, the near-vision sighting position (visual line position) at the left eye side is adjusted so as to finish positioning of the sighting positions (visual line positions) for both eyes.

Subsequently, the operation for inputting the positional relationship of the spectacle frame by the inspector is started when the progress switch 13c is pressed. As shown in FIG. 2, cross lines comprising a lateral line 42 and a longitudinal line 43 are displayed on the displays 1R, 1L, respectively. A voice command that "Adjust the cross lines so as to coincide with the internal periphery of the right eye frame by tilting the lever, and press the progress button" is given from the voice generating part 21. Since the lateral line 42 moves in the vertical direction by the display control of the control part 20 when the lever 12 is tilted in the vertical direction, the inspector disposes the lateral line 42 coinciding with the upper internal periphery of the right eye frame while observing the line and the spectacular frame for the right eye observed through the display 1R. Moreover, since the longitudinal line 43 moves in the horizontal direction by the display control of the control part 20 when the lever 12 is tilted in the horizontal direction, the longitudinal line 43 is disposed coinciding with the nose side internal periphery of the right eye frame. When the progress switch 13c is pressed, a voice command for adjusting the cross lines coinciding with the left eye frame is given so that the inspector disposes the lateral line 42 and the longitudinal line 43 coinciding with the internal periphery of the left eye frame in the same manner.

In the case the positions of the frame F and the displays 1R, 1L may be displaced during the operation, it can be executed as follows. That is, in addition to the display of the lateral line 42 and the longitudinal line 43, the light transmission hole 40 pattern (in this case, a frame display can be used) is displayed at the eye point measuring positions on the displays 1R, 1L at the same time. Then, the inspector executes the input operation of the positional relationship of the frame F while confirming whether the light transmission hole 40 pattern is not displaced to the subject. Moreover, it is also effective to execute the input of the positional relationship of the frame F before positioning of the transmission hole 40 by the subject, and to confirm whether the positioned lateral line 42 and longitudinal line 43 are not displaced with respect to the frame F during the operation for determining the eye points by the subject.

When the positional relationship of the frame F is inputted on the display 1R, 1L surface, the eye point measurement results are shown on the display part 11 (see FIG. 2). On the screen 50 of the display part 11, are displayed a left eye PD, a both eye PD, and a right eye PD as far-vision PDs in the display item 51. These are provided from the positions of the coordinates of the light transmission hole 40 disposed on the sighting positions (visual line positions) of both eyes in the far-vision measurement.

In the display item 52 there below, are shown distances of the far-vision eye points for the right and left eyes with respect to the nose side internal periphery of the frame F. In the display item 53, are shown distances of the far-vision eye points for the right and left eyes with respect to the upper internal periphery of the frame F.

Similarly, in the display item 54 are displayed a left eye PD, a both eye PD, and a right eye PD, provided from the positions of the coordinates of the light transmission hole 40 disposed on the sighting positions (visual line positions) in the near-vision measurement. In the display item 55 and 56 are shown distances of the near-vision eye points with respect to the internal periphery of the frame F.

Since the sighting positions (visual line positions) can be determined based on the confirmation by the subject himself as mentioned above according to the device, in addition to the far-vision and the near-vision points, the points in the middle range can also be determined. For example, with the light transmission hole 40 displayed 2 mm below the far-vision eye point, the sighting position (visual line position) is determined according to operation of the lever 12 in the horizontal direction. According to the input signal of the progress switch 13c, the control part 20 stores the position. By repeating the operation with the light transmission hole 40 displayed downward by 2 mm each time, the measurement data of the middle range points from the far-vision eye points to the near-vision eye points can be obtained, and the measurement data can be confirmed by the printing output or display on the display part 11 (the measurement mode can be selected by the mode switch 13a).

Figure 4:
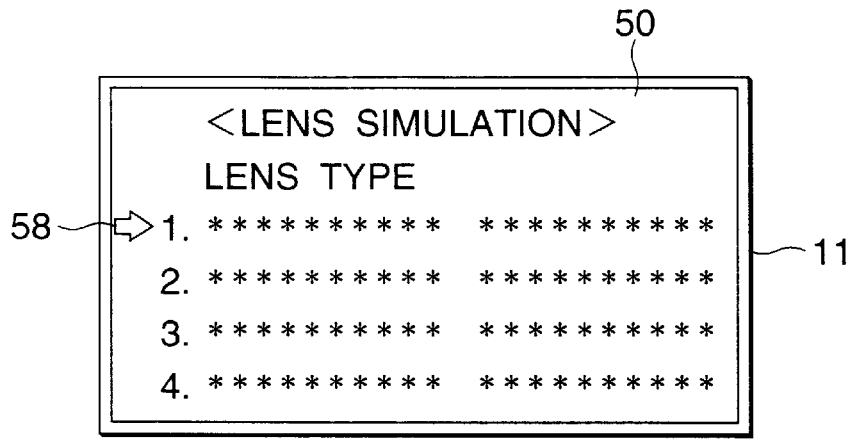
FIG. 4 is a diagram showing an example of a display screen in a lens simulation mode.

Next, the simulation mode for confirming the viewing state of various patterns of a progressive lens will be explained. According to press of the mode switch 13a, it is switched to the lens simulation mode. As shown in FIG. 4, the screen 50 of the display part 11 is switched to the lens simulation mode screen, with the manufacturer's name and the model name of the progressive lens displayed as the type thereof. The progressive lens can be selected by moving a cursor 58 displayed at the left side according to operation of the lever 12 in the vertical direction (lens types are displayed successively by scrolling in the vertical direction).

Figure 5:
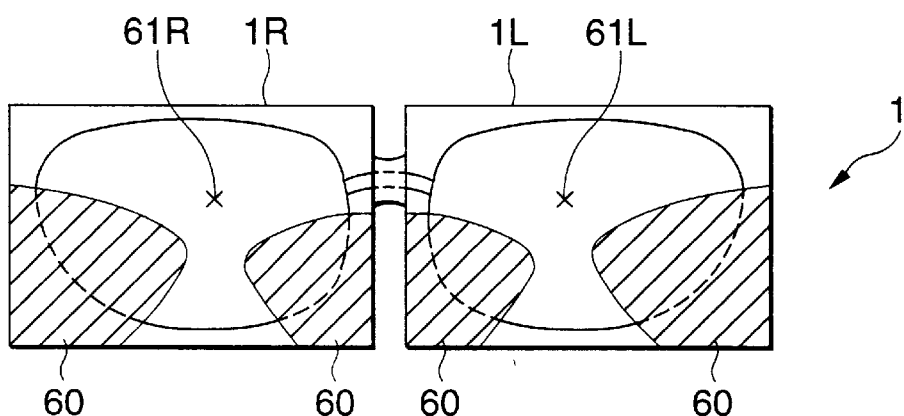
FIG. 5 is a diagram showing an example of an optical pattern of a progressive lens displayed on a liquid crystal display in the lens simulation mode.

When the lens type is selected, an optical pattern according to the progressive lens type is formed and displayed on the displays 1R, 1L as shown in FIG. 5. The hatched region 60, which shows the region wherein an image is distorted by drastic change of the cylindrical degree and the axial angle, is shown as a half-transmittable part on the displays 1R, 1L. In contrast, the far-vision portion, the progressive portion and the near-vision portion in the progressive lens are formed as a transmittable region. According to the shape of the hatched region 60, the progressive lens pattern is formed so that the position of the pattern on the displays 1R, 1L is determined based on the measured far-vision eye points 61R, 61L. The progressive lens pattern information is stored in the memory 23 for each lens of various manufacturers. By selecting the lens type at the control part 10 side, the pattern can be simulated on the displays 1R, 1L. The subject can perceive the range wherein an image can be observed without distortion as well as can understand the characteristics of the progressive lens by the observation of the chart through the displays, and thus it can be utilized for selection of the progressive lens.

Figure 6:
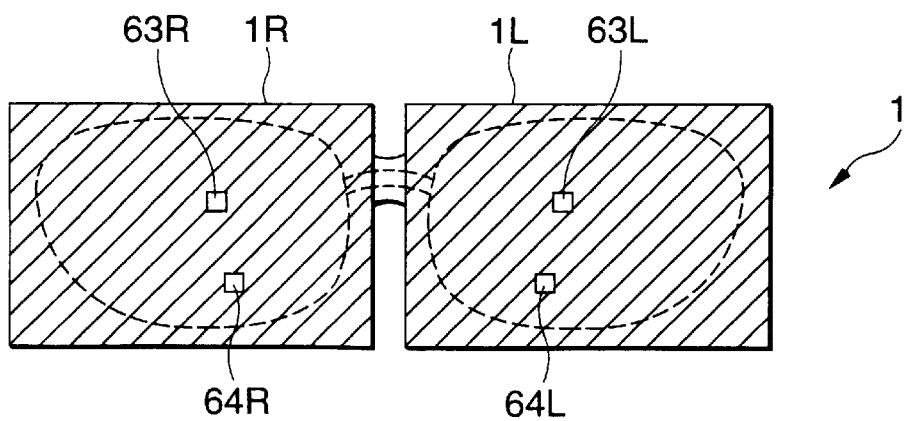
FIG. 6 is a diagram showing a modified example of an optical pattern of a progressive lens displayed on the liquid crystal display in the lens simulation mode.

Moreover, the progressive lens viewing condition can be simulated as follows. FIG. 6 is a display style of the far-vision eye points and the near-vision eye points according to the progressive lens type. On the displays 1R, 1L are formed transmission windows 63R, 63L showing the far-vision points at the far-vision eye point positions obtained by the eye point measurement and the transmission windows 64R, 64L showing the near-vision points at the near-vision eye point positions (the other region is in the half-transmittable state). The positions for forming the transmittable windows 64R, 64L are determined based on the positional relationship with respect to the far-vision points for each lens type. The position of the near-vision point in a ready-made progressive lens is determined, for example, at a position downward by 14 mm and to the nose side by 2 mm with respect to the far-vision point. The optical pattern information of the far-vision and near-vision points is stored in the memory 23 for a large number of lens types so that the lens type can be selected by the control part 10 for simulation as mentioned above so as to select the one most suitable for the subject. In this case, if the near-vision eye point positions are already found by the eye point measurement, it is possible to select the lens based thereon, but it is also possible for the subject to select then one he likes by comparing the viewing conditions according to examination of the viewing conditions through the far-vision point transmittable windows 63R, 63L and the near-vision point transmittable windows 64R, 64L.

The above-mentioned progressive lens information can be stored not only in the memory 23. By connecting a memory card reader 35 for inserting a memory card 36 so that the lens pattern information can be read out and inputted again, new information and a large number of data can easily dealt with.

The results of the measurement of the eye points and the selected progress lens type as mentioned above (the ones finally indicated are the results) are printed and outputted from the printer 14 by pressing the print switch 13*d*. Moreover, in the case an external device 37 such as a computer is connected with the connector 15, the data are transferred also to the external device 37 side.

The measurement data measured in the eye point measuring mode are not necessarily used in the progressive lens viewing condition simulation. By inputting the eye point data from the external device 37 to the control part 10 side, the optical pattern of the progressive lens can be formed before the eyes of the subject based on the data. That is, it can also be provided independently as a progressive lens pattern confirming device.

Figure 7:
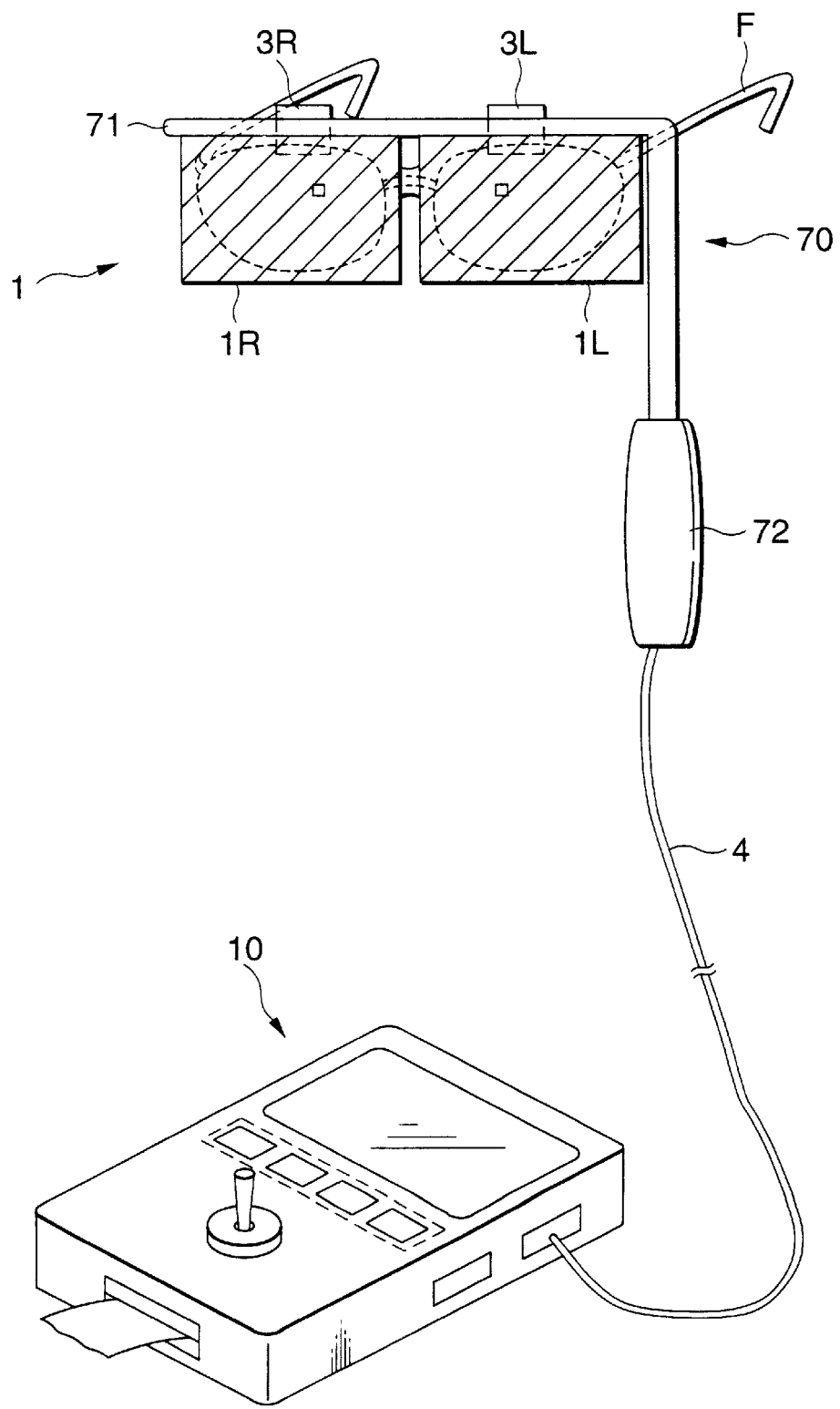
FIG. 7 is a diagram showing an example of a holding mechanism for supporting the weight of the liquid crystal display by the subject.

Although the panel part 1 of this embodiment is provided as a type directly mounted onto a spectacular frame, any one with the displays 1R, 1L disposed at the front side of the spectacular frame (preferably at a position immediately before the frame) can be used, and thus in the case the installation is difficult due to the reasons such as the weight of the liquid crystal displays and the spectacular frame shape, a goggle type or a type fixed on the head can also be adopted. Moreover, as shown in FIG. 7, it is also effective to attach a holding mechanism 70 for supporting the weight of the liquid crystal displays by the subject. A horizontal bar 71 for supporting the panel part 1 (displays 1R, 1L) elongates downward at the right end, with the lower end attached with a grip 72. Similar to the above-mentioned embodiment, the frame F and the displays 1R, 1L are fixed by the mounting members 3R, 3L, and the subject holds the grip 72 for supporting the panel part 1 for executing the measurement.

As heretofore explained, according to the invention, the subjective eye points confirmed by the subject himself can easily be measured without the need of a long time. Since the operation is facilitated so as to enable the measurement by the subject himself and the operation procedure is instructed by the voice guide, the eye points desired by the subject himself can be determined. Furthermore, owing to the simple configuration, an inexpensive and compact device can be realized.

Moreover, since the optical pattern of various progressive lenses can be formed in front of the eyes of the subject for easily confirming the viewing condition, the subject can easily understand the characteristics of the progressive lenses so that it can be utilized for selection of the progressive lens.

<Embodiment 2>

Figure 8A:
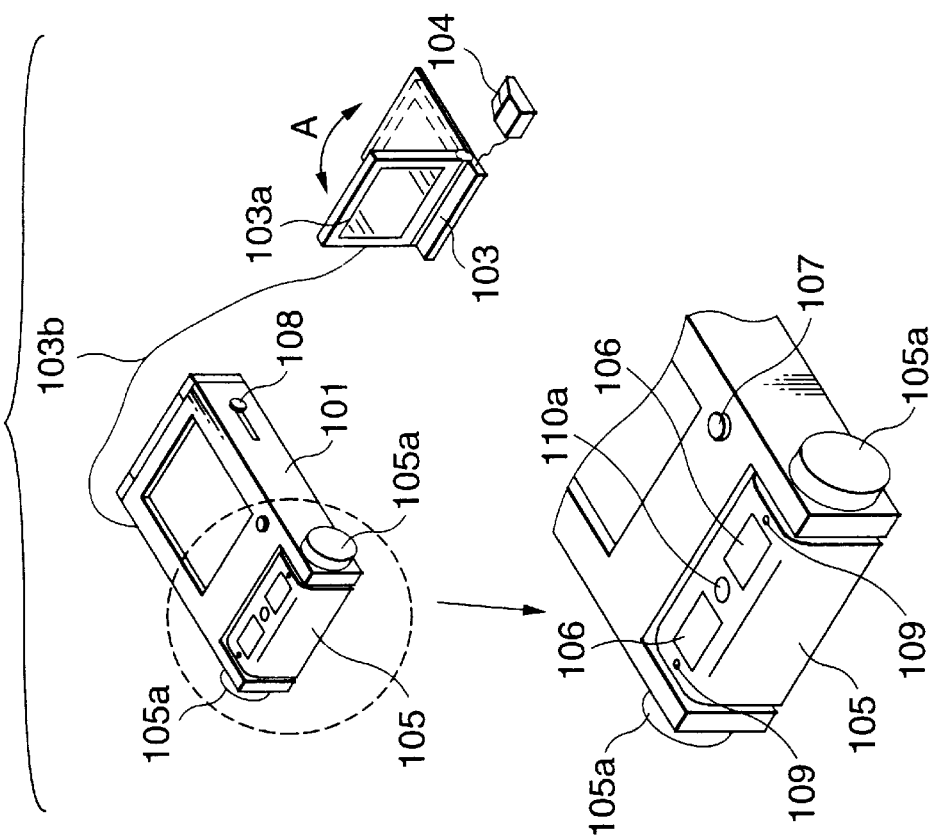
FIGS. 8A and 8B are diagrams showing the external appearance of a device according to a second embodiment.
Figure 8B:
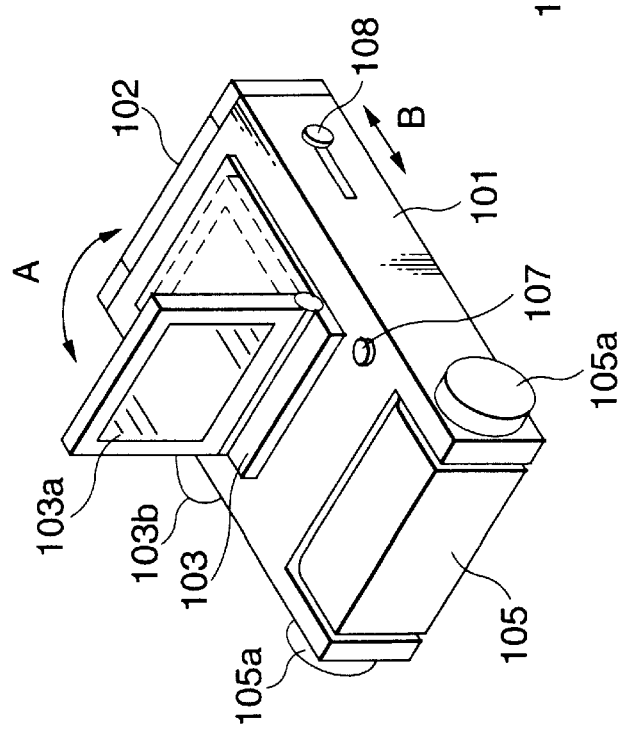
Figure 9:
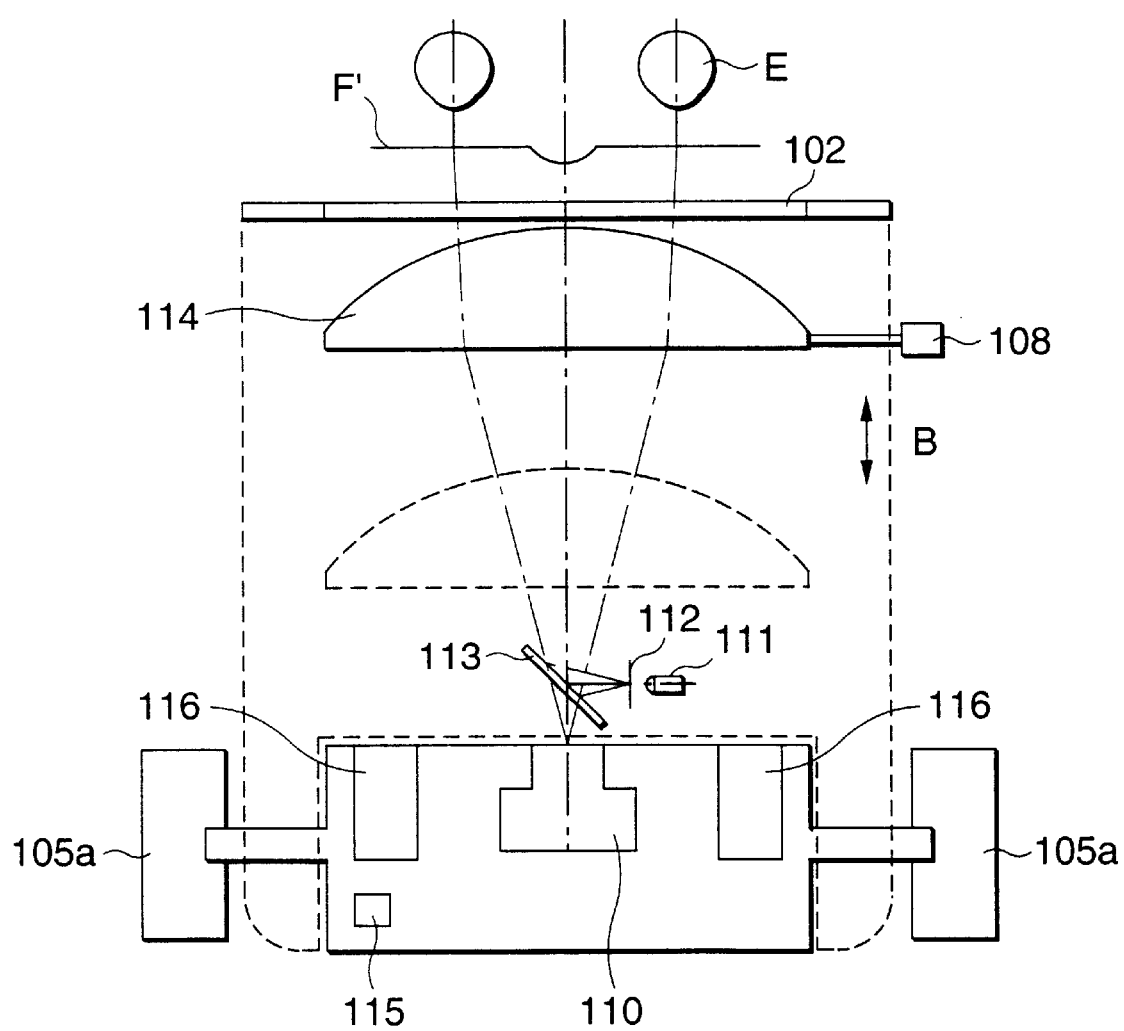
FIG. 9 is a diagram showing the schematic configuration of the optical system of the device according to the second embodiment.

Another embodiment of the invention will be explained with reference to the drawings. FIGS. 8A and 8B are diagrams showing the external appearance of a device according to a second embodiment. FIG. 9 is a diagram showing the schematic configuration of the optical system to be disposed in the device.

Numeral 101 is a device main body, with a measuring window 102 provided at the side facing to the subject. Numeral 103 is an image display part, wherein an image photographed by a television camera 110 and measurement information are displayed on a display 103*a*. As the display 103*a*, a commonly used LCD can be used. Moreover, the display 103*a* can be tilted in the arrow A direction so as to be used portably. As shown in FIG. 8B, the display part 103 can be used in the detached state. The display part 103 and the main body 101 are connected by a connecting cable 103*b*. Numeral 104 is a mouse connected with the display part 103 so as to be used as a pointing device.

Numeral 105 is a photographing part comprising the camera 110, distance sensors 116, and a tilt sensor 115 provided in the housing as shown in FIG. 9. The photographing part 105 can be rotated according to operation of rotation knobs 105*a* disposed at both side surfaces of the main body 101. In measurement in a near-vision distance, as shown in FIG. 8B, the camera 110 is separated from a photographing optical system described later by the rotating operation so that the photographing opening 110*a* of the camera 110 faces to the upper surface side of the main body 101. Accordingly, the photographing operation can be enabled with the camera 110 alone without using the photographing optical system in the main body 101 (details will be explained later).

Moreover, the photographing part 105 can be rotated such that the photographing opening 110*a* faces to the bottom surface side of the main body 101. In the case it is rotated so as to have the photographing opening 110*a* facing to the bottom surface side, the photographing operation can be executed with the main body 101 upright vertically by tilting the display 103*a*. Furthermore, the photographing part 105 can be separated from the housing of the main body 101 without separating by the rotating operation. Mirrors 106 are provided at both sides of the photographing opening 110*a* so that the mirrors 106 can be used by the subject for disposing the photographing optical axis of the camera 110 coinciding with his sight. Numeral 109 is an input window for the distance sensors 116. Numeral 107 is a photographing switch.

In FIG. 9, numeral 111 is a chart (index) illuminating lamp, and 112 is a chart (index) plate having a spot opening. The lamp 111 illuminates the chart (index) plate 112 to serve as a gazing target from the back side. Numeral 113 is a half mirror. Numeral 114 is a convex lens with a size enabling the subject to gaze the chart (index) plate 112 with both eyes. Moreover, the convex lens 114 can be moved in the optical axis direction (B direction) thereof by a knob 108 so that the optical distance between the measuring window 102 and the chart (index) plat 112 can be changed from 300 mm to the infinity. The lamp 111 to the convex lens 114 comprise a gazing target presenting optical system for disposing the gazing target to be gazed at by the subject's eyes.

The photographing part 105 comprising the camera 110 as the photographing means is provided behind the half mirror 113. The camera 110 is disposed on the optical axis of the convex lens 114 as well as at the substantially optically same position with respect to the chart (index) plate 112. The convex lens 114 and the camera 110 comprise a photographing optical system for photographing the face of the subject. The subject gazes at the chart (index) plate 112 with both eyes via the measuring window 102. The gazing distance can be changed optically to the distance desired by the subject according to movement of the convex lens 114. At the same time, the position of the camera 110 is at the substantially optically same position with respect to the chart (index) plate 112. That is, according to the configuration, the television camera 110 can photograph the front side subject eyes from the sight direction (visual line direction) of the subject's eyes with the same distance with the gazing distance.

Moreover, the two distance sensors 116 are provided at both sides of the camera 110 in the photographing part 105 so that the distance from the subject's eyes (spectacular frame worn by the subject) to the camera 110, that is, the gazing distance can be detected. In measurement, a scale auxiliary tool 120 (details will be described later) shown in FIG. 10 is mounted on the spectacular frame F. The scale auxiliary tool 120 comprises an LED 123 for emitting an infrared ray. A light from the LED 123 is inputted to the distance sensors 116 via the measuring window 102, and the convex lens 114. The distance sensors 116 comprise a collecting lens and a position detecting element. The light input position to the position detecting element varies depending on the distance change of the camera 110 (distance optically changed according to movement of the convex lens 114). From the position change, the distance of the camera 110 position (gazing distance) is detected. In the case the photographing part 105 is used with rotation the light from the LED 123 is incident on the distance sensors 116 directly so that the camera 110 position can be detected.

The camera 110 comprises an auto focus mechanism for automatically focusing to a subject image according to a lens disposed in the inside thereof, and an auto zoom mechanism for automatically zooming the subject image so as to be displayed with a certain size on the display 103a. In the auto zoom mechanism, a calculation control part 130 described later controls the zoom mechanism based on the distance information of the distance sensors 116. Moreover, in the case it exceeds the limit of the optical zoom, the digital zoom is executed by an image process.

Numeral 115 is a tilt sensor for detecting the tilt angle of the photographing optical axis of the camera 110. The angle information obtained by the tilt sensor 115 is displayed on the display 103a. The angle information is utilized in calculation of the angle adjustment of the main body 101, the downward swaying angle of the eye balls or the face tilt angle by the near-vision eye position.

Figure 10A:
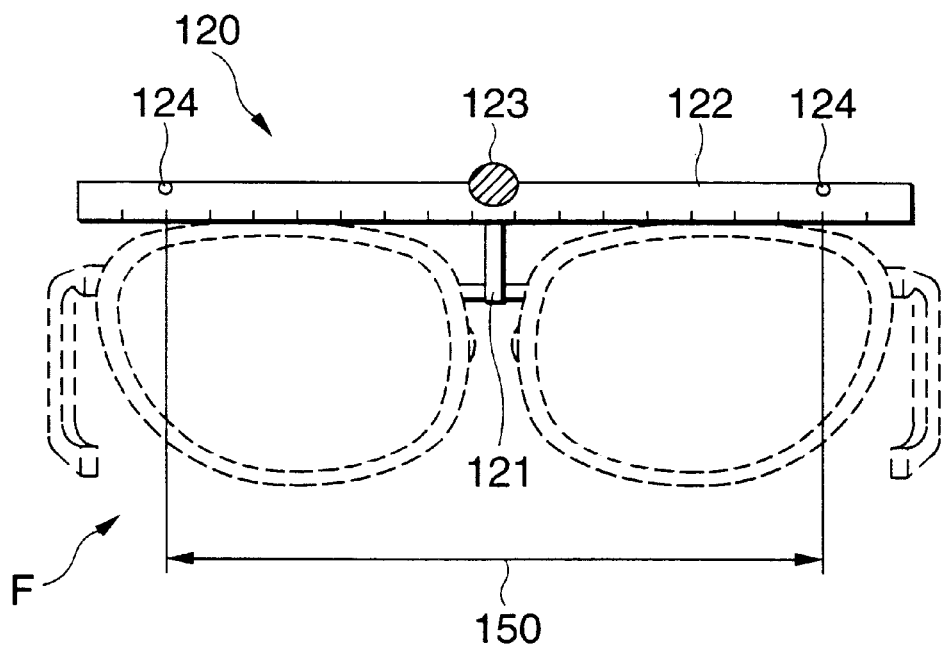
FIGS. 10A and 10B are diagrams showing a scale auxiliary tool.
Figure 10B:
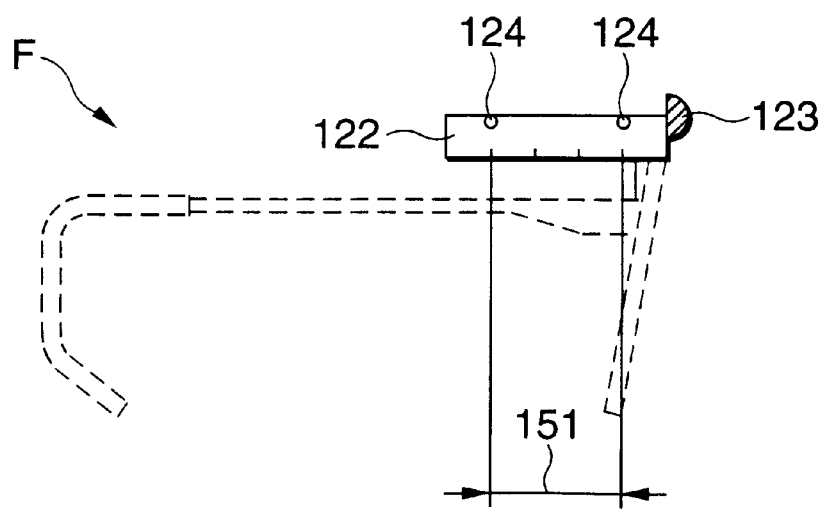

FIG. 10A is a schematic external appearance plan view of a scale auxiliary tool to be used for detecting the eye position or the distance, and FIG. 10B is a side view thereof.

The scale auxiliary tool 120 can be mounted on the bridge upper part of the spectacular frame F selected by the subject by a mounting metal fixture 121. Numeral 122 is a U-shaped scale plate, with graduations applied on the plate elongating from the front side surface to both side surfaces so that the actual length can be visibly observed. Numeral 124 is the reference point to be the reference of the measured distance, provided at 6 points including 2 each points on the front side and the right and left sides on the scale plate 122. The distance 150 between the two points on the front side surface, and the distance 151 between the two points on both side surfaces are preliminarily set at known distances, such as 100 mm and 20 mm. The distances 150, 151 between the reference points 124 are used as the reference distances for detecting the size of the spectacular frame taken into the image data. Numeral 123 is an LED for emitting an infrared ray. As mentioned above, it is used for finding the distance between the gating point and the subject's eyes E.

Figure 11:
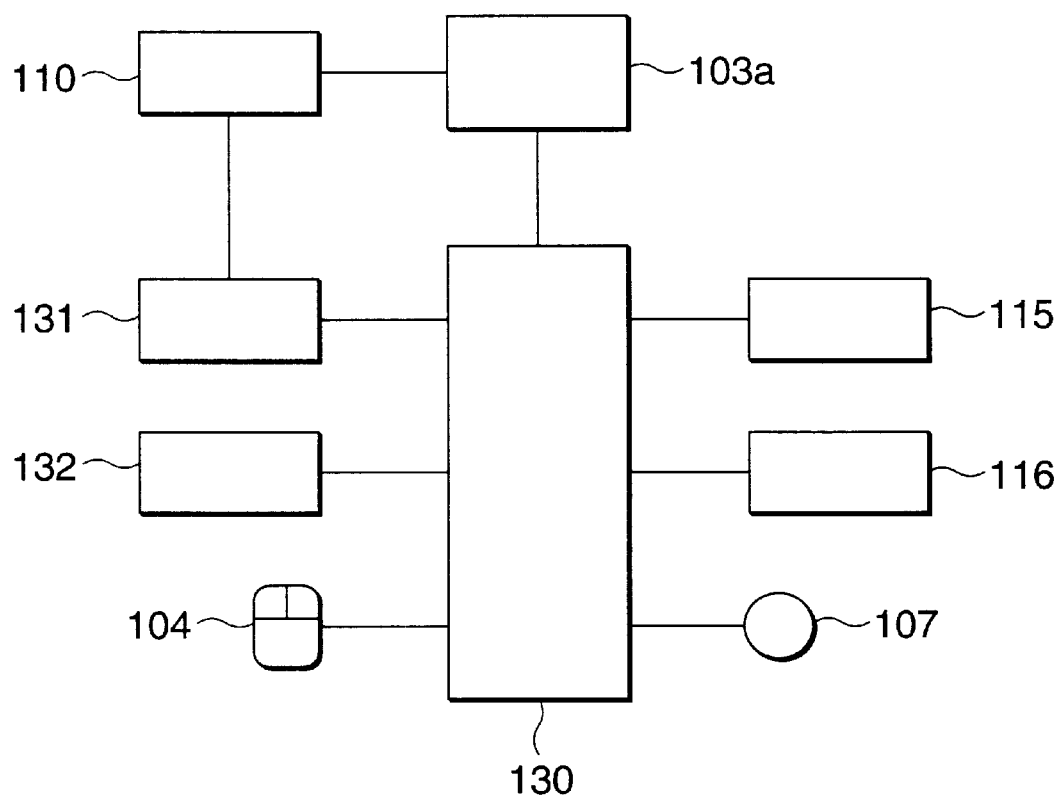
FIG. 11 is a block diagram showing the control system of the device according to the second embodiment.

The measuring operation in the device with the above-mentioned configuration will be explained with reference to the block diagram of the control system shown in FIG. 11. Here, the measurement in adjusting a progressive lens will be explained in three parts including the far-vision measurement for measuring the eye points when the subject's eyes look at a far point (or a middle point), the side measurement for measuring the forward tilting angle of the spectacular frame, and the near-vision measurement for measuring the eye points at a short distance.

First, the spectacular frame F is put on the subject and the wearing state of the frame F is adjusted so as to fit to the subject's face. Then, the scale auxiliary tool 120 is mounted on the frame F selected by the subject as shown in FIGS. 10A and 10B. In order to have the scale auxiliary tool 120 parallel with the frame F, the lower end of the scale auxiliary tool 120 is contacted with the upper end of the spectacular frame F.

<Side measurement>

The measurement is executed for finding out the forward tilting angle of the worn spectacular frame, and the inter-vertex distance between the spectacular frame and the corneal vertices.

Figure 12:
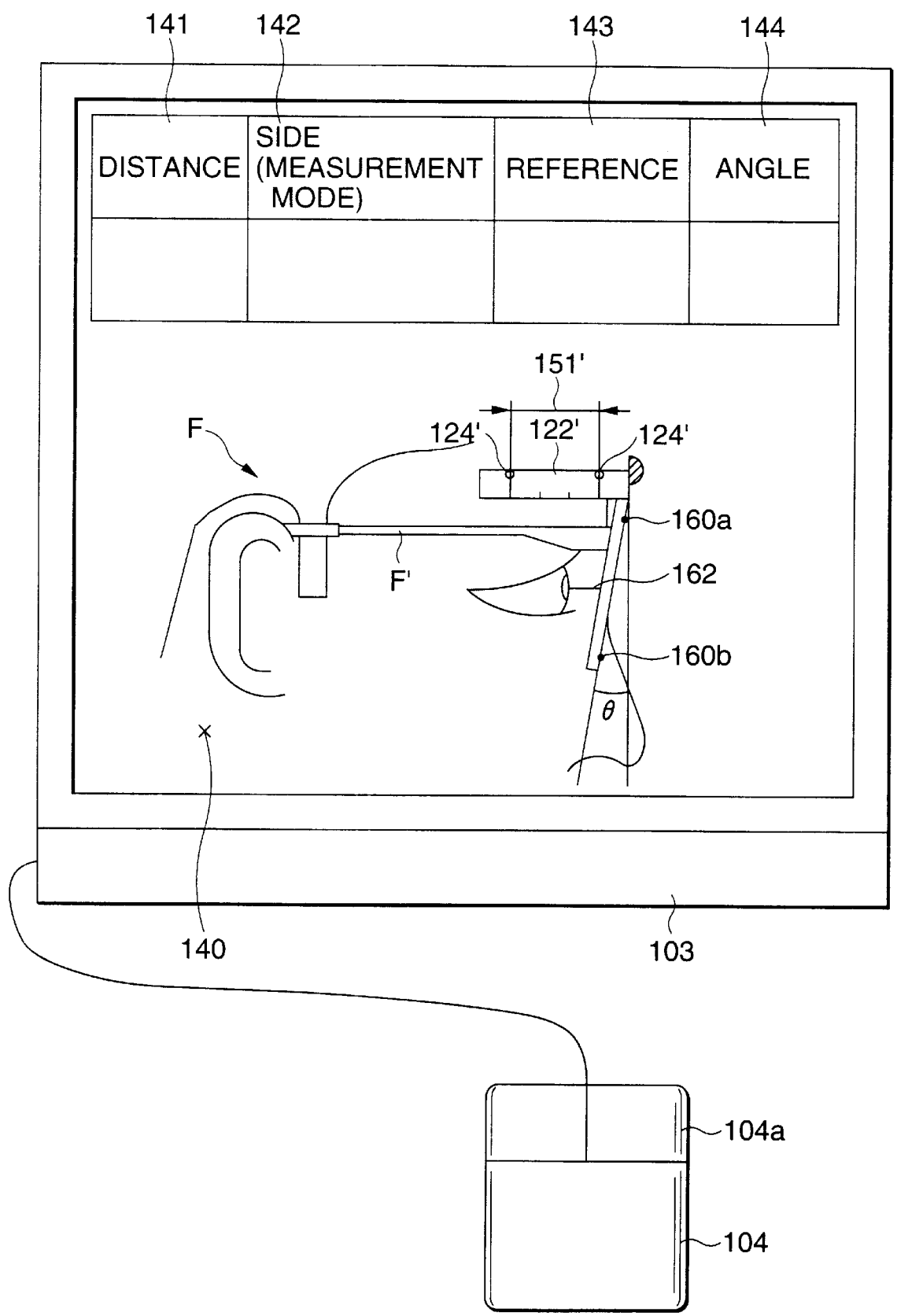
FIG. 12 is a diagram showing an example of an image stored in a memory.

The measurement mode is set to be the side measurement mode by the display 103a. As shown in FIG. 12, the mode is set by moving a cursor mark 140 by the mouse 104 to a side measurement mode item 142 and pressing a button 104a. It is also possible to select items by a touch panel method or a touch pen without using the mouse 104.

After selecting the side measurement mode, the inspector takes the main body 101 on his hand so as to direct the measuring window 102 to the side part of the subject's face (or rotates the photographing part 105 to the bottom surface side of the main body by 90 degrees for directly photographing with the camera 110) for determining the position thereof such that the face side part of the subject with the frame F on can be projected on the display 103a. When the main body 101 position is determined, the switch 107 is pressed. When the switch 107 is pressed, the calculation control part 130 stores the face side part picture of the subject in a memory 131 as the image data.

FIG. 12 is a diagram showing an example of an image stored in the memory 131. In the side measurement mode, measurement results of forward tilting angle $\theta$ and the inter-vertex distance 162 are obtained as follows. First, after selecting the reference measurement item 143 on the screen by the mouse 104, the cursor mark 140 is moved so as to designate two reference point images 124', on the scale plate image 122' (with the cursor mark 140 placed on the reference point images 124', the button 104a is pressed). Subject to the designation by the cursor mark 140, the calculation control part 130 calculates the angle formed by the straight line linking the two points of the reference point images 124' and the horizontal line on the display 103a (hereinafter referred to as the reference angle) so as to be stored in a memory 132. Furthermore, since the distance 151 between the two points as the reference points 124 applied on the scale pate 122 is determined preliminarily, the calculation control part 130 compares the distance 151 and the distance 151' for calculating the correction ratio.

Next, the angle detection item 144 is selected for finding out the angle formed by the vertical plane with respect to the horizontal sight (visual line) and the lens surface (forward tilting angle) θ. The inspector places the cursor 140 on the front frame of the spectacular frame image F' and designate optional two points 160a, 160b, respectively. The calculation control part 130 calculates the angle formed by the straight line linking the two points (160a, 160b) and the straight line linking the designated reference points on the scale plate 122'. From the calculated angle, the forward tilting angle θ is calculated so that the value thereof is stored in the memory 132 as well as the angle is displayed on the display 103a.

Moreover, in the case of finding the distance from the corneal vertex to the inside of the frame F (inter-vertex distance 162), after selecting the distance measurement item 141, the corneal vertex image and the inside of the frame F disposed in the horizontal direction thereof are designated by the cursor mark 140, respectively for finding out the distance 162. From the obtained distance 162 and the calculated correction ratio, the actual distance is calculated. Utilizing the obtained inter-vertex distance, for example, in the case it is not a general inter-vertex distance (12 mm), the spectacular can be adjusted again such that the inter-vertex distance can be 12 mm. Moreover, in the case of improving the correction effect by changing the inter-vertex distance intentionally, it can also be used as a means for calculating change of the correction effect according to the obtained inter-vertex distance.

<Far-vision measurement>

The inspector confirms preliminarily the far-vision distance in use desired by the subject. The inspector sets the far-vision measurement mode by the measurement mode item 142 on the display 103a, and with the main body 101 on hand, disposes the measuring window 102 at a position about 10 cm away from the eyes of the subject. The subject is instructed to look at a light on the chart (index) plate 112, which is the gazing target, via the measuring window 102. The front eye part of the subject is photographed by the camera 110 of the photographing optical system so as to e displayed on the display 103a. The inspector adjusts the main body 101 minutely such that the front eye part image of the subject can be displayed in the vicinity of the center of the display 103a while observing the display 103a. Since the distance detected by the distance sensors 116 is displayed on the display 103a, the convex lens 114 is moved and adjusted according to operation of the knob 108 such that the displayed distance is equal to the gazing point distance preliminarily confirmed to the subject. Moreover, since the tilt angle detected by the tilt sensor 115 is displayed on the display 103a, the main body 101 is maintained horizontally while observing the tilt angle.

When the photographing position is adjusted according to observation of the display 103a, the front eye part image of the subject with the frame F on is stored in the memory 131 as the image data by the photographing switch 107.

Figure 13:
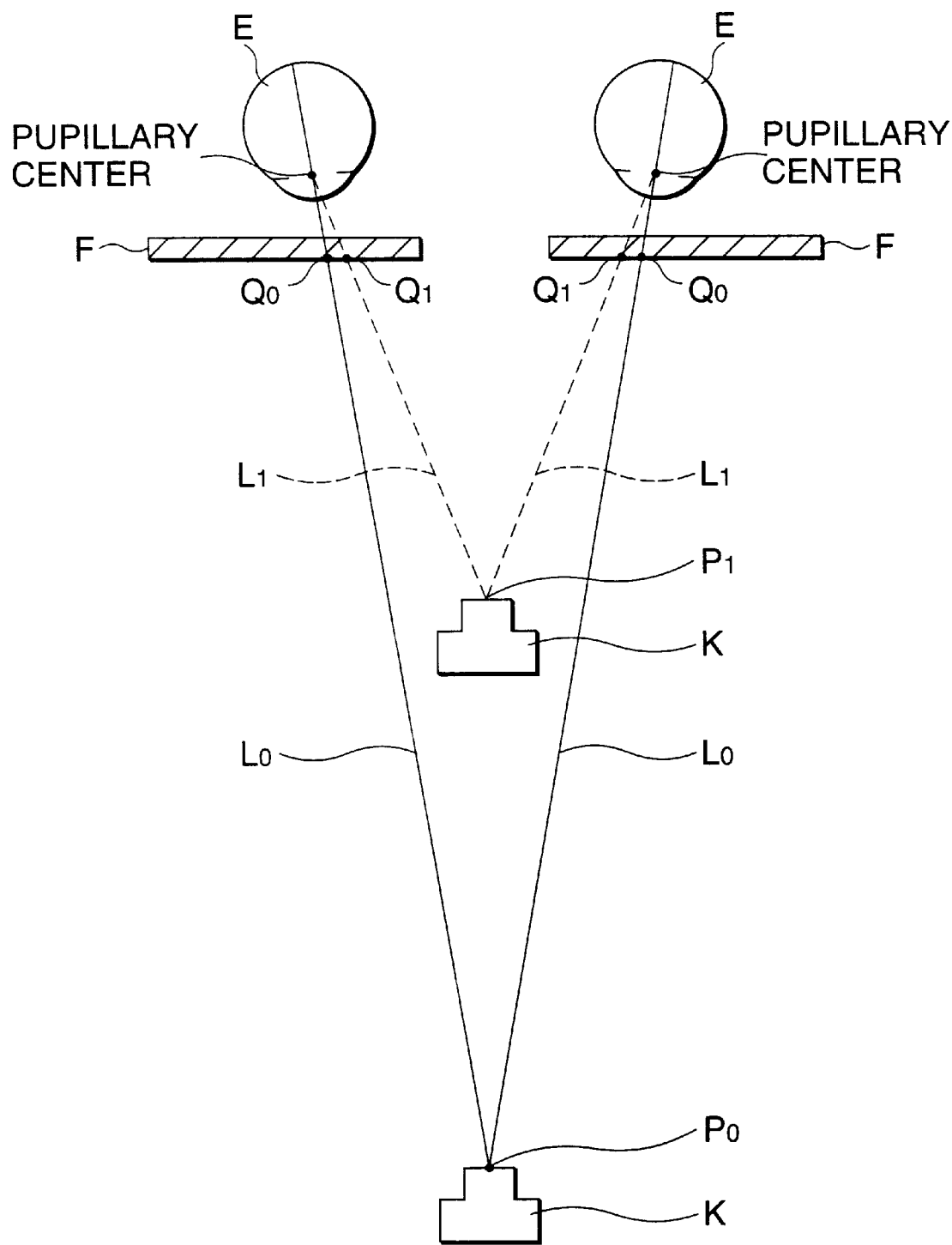
FIG. 13 is a diagram showing the reason why the eye points differ depending on the photographing position.

As mentioned above, since the device of the invention photographs the subject's eye image with the camera 110 disposed at the substantially optically same position with respect to the gazing target position, the eye points can be measured accurately. The reason will be explained with reference to FIG. 13. When the subject's eyes E gaze at the gazing target $P_0$ disposed at a desired distance, the sight directions (visual line directions) through the frame F are as shown by the solid lines $L_0$. Since the eye points are the positions of the sight (visual line) passing through on the frame F, the points $Q_0$ on the figure are the accurate positions. In the case the subject's eye image including the frame F is photographed by a camera K disposed at a position $P_1$ with a distance different from the gazing target $P_0$, the pupillary center positions are photographed as in the directions shown by dot lines $L_1$. Therefore, the pupillary center positions with respect to the frame F are measured to be on the points $Q_1$ on the frame F shown in the figure, which are displaced from the points $Q_0$. In contrast, by disposing the camera k at the gazing target $P_0$ position, the pupillary centers can be photographed as on the solid lines $L_0$ showing the sight directions (visual line directions), and thus the points $Q_0$ on the frame F can be measured accurately.

FIG. 14A is a diagram for explaining the method for finding the far-vision eye points and the PD from the image data shown on the display 103a. After selecting the reference measurement item 143 displayed on the display 103a, the inspector moves the cursor mark 140 onto the two reference point image 124' for designation. Since the distance 150 between the two reference points 124 applied on the front surface of the scale plate 122, based on this and the distance 150' between the two reference point images 124', the correction ratio of the photography magnification for finding out the eye points and the actual distance of the PD is calculated. Moreover, according to the designation of the two reference point images 124', the tilt angle of the photographed image with respect to the right and left direction can be corrected (with the display 103a image disposed horizontally based on the tilt angle information, the measurement described later can be facilitated).

Next, the distance measurement item 141 is selected or finding out the far-vision PD. The cursor mark 140 is moved by the mouse 104 for designating the pupillary center points $C_R$ and $C_L$ of the front eye part image displayed on the display 103a, respectively. Accordingly, the horizontal reference line $X_R$ and the vertical reference line $Y_R$ centering on the pupillary center point $C_R$ are indicated, moreover, the horizontal reference line $X_L$ and the vertical reference line $Y_L$ centering on the pupillary center point $C_L$ are indicated. The actual distance of the far-vision PD can be calculated by correcting the distance 151 between the reference line $Y_R$ and the reference line $Y_L$ according to the correction ratio. The calculated actual distance of the far-vision PD is stored in the memory 132 as well as displayed on the display 103a (not illustrated).

Furthermore, a single eye PD can be found out as follows. Similar to the above case, the two reference point images 124' and the pupillary center point $C_R$ are designated preliminarily. Then, the intersections 172, 176 at which the horizontal reference line $X_R$ obtained by designating the pupillary center point $C_R$ intersects with the right and left inner frames, are designated. Accordingly, the middle point of the intersection 172 and the intersection 176 can be found. The middle point is the point dividing the frame in two (center of the face). Therefore, by finding out the distance from the pupillary center point $C_R$ to the middle point, the right eye side single eye PD can be obtained. The left eye side single eye PD can be obtained by subtracting the right eye side single eye PD from the PD.

The pupillary centers can also be detected automatically by image process. A light from the chart (index) plate 112 is directed to the subject's eyes gazing at the chart (index) plate 112 so that the corneal luminescent spots thereof are formed on the corneal vertices. Since the corneal vertices can substantially be regarded as the pupillary centers, the pupillary center position data can be obtained by the detection process of the luminescent spots from the front eye part image.

For the eye point measurement, the measurement item 145 is selected. The cursor mark 140 is moved onto the positions of the intersections of the reference lines and the right and left inner frames of the frame image F' 170 to 175 for designation. From the position data of the intersections 170 to 175 designated by the cursor mark 140, the far-vision eye positions (actual distance) of the subject's eyes with respect to the actual frame F can be obtained by the correction ratio of the photography magnification and the size correction in consideration of the forward tilting angle obtained by the side measurement (not illustrated).

Figures 17A, 17B:
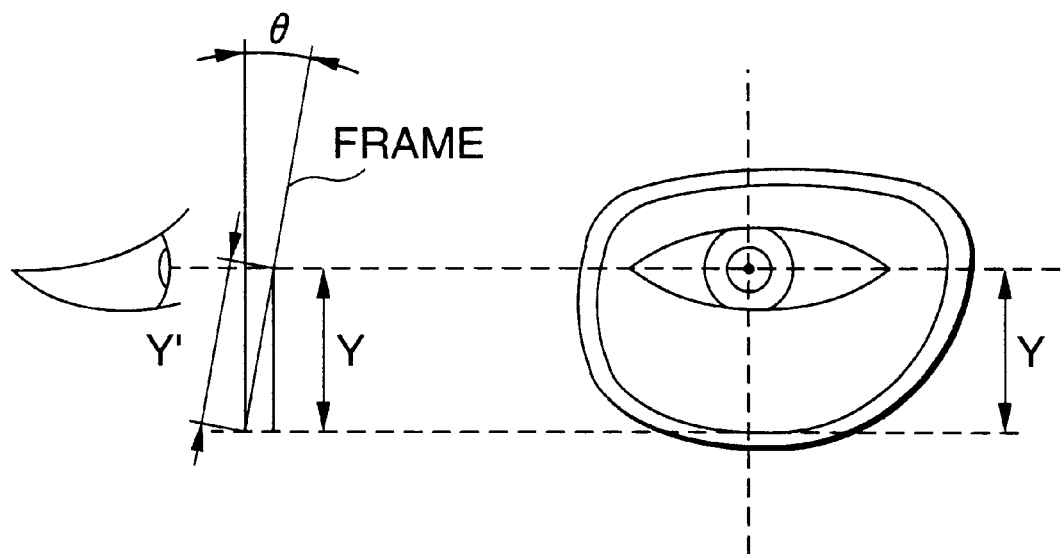
FIGS. 17A and 17B are diagrams for explaining the size correction.

FIGS. 17A and 17B are diagrams for explaining the size correction in the upper and lower direction. Since the distance Y obtained by the far-vision measurement as shown in FIG. 17B differs from the actual distance Y' because the frame F tilted with a forward tilting angle θ is viewed from the front side. Therefore, by using a trigonometric function, $Y'=Y/(\cos \theta)$, the actual distance can be found.

Figure 18:
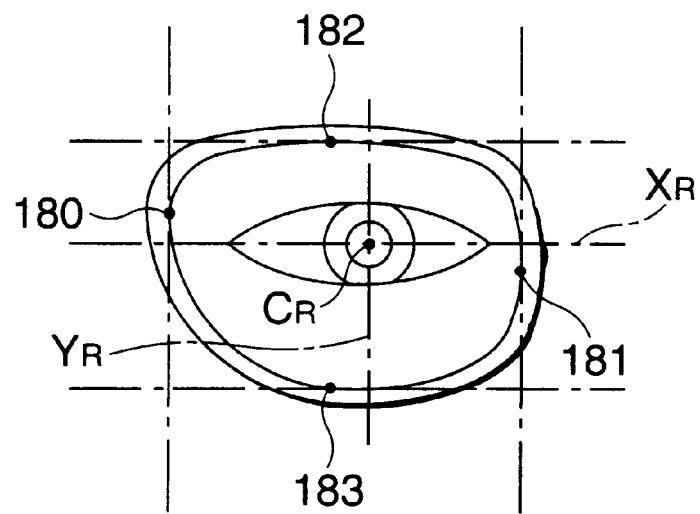
FIG. 18 is a diagram for explaining the boxing system.

The eye points can also be measured as the position data of the pupillary centers with respect to the left end, right end, upper end and lower end of the frame shape as shown in FIG. 18 (only the right frame is shown in the figure). In this case, the horizontal and vertical reference lines $X_R$, $Y_R$ are dragged by the mouse 104 for designating the left end 180, the right end 181, the upper end 182 and the lower end 183 with respect to the frame inner side. Based on this and the preliminarily designated pupillary center $C_R$, the pupillary center position with respect to the frame can be calculated.

Moreover, in the case the gazing point target distance is set at a middle distance (for example, 10 m) instead of the infinity in the far-vision measurement, the measurement can be executed further accurately with the main body 101 tilted with an angle such that the sight (visual line) can be slightly downward instead of maintaining the main body 101 horizontally. Since the tilt angle can be found out from the height of the eyes of the subject, the gazing point position and the distance with respect to the gazing point, the main body 101 is to be tilted until the tilt angle of the device main body 101 obtained by the tilt sensor 115 can be a desired angle.

Figure 15:
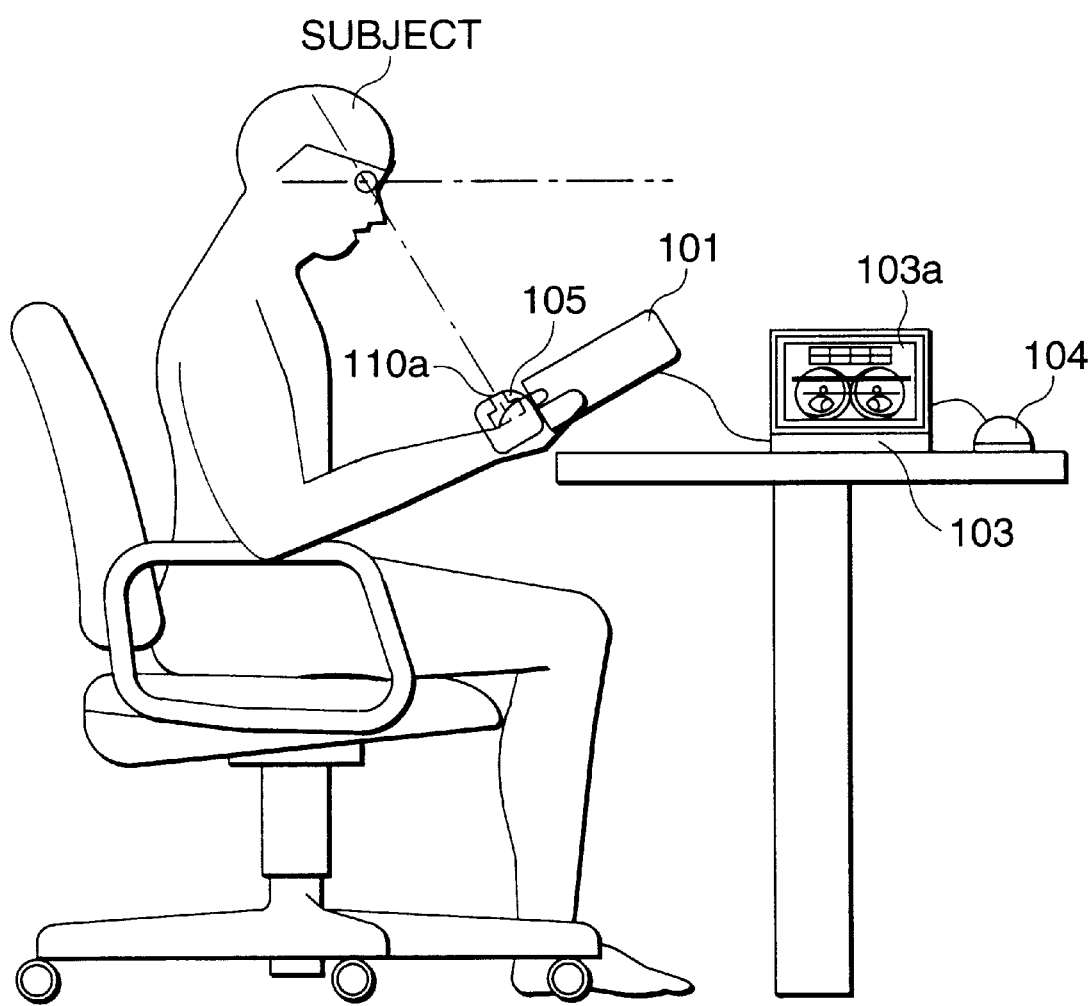
FIG. 15 is a diagram showing an example of use of the device main body in measuring the eye points for the near vision.

<Near-vision measurement>The measurement mode item 142 is set at the near-vision measurement mode. In the case of the near-vision measurement, as shown in FIG. 15, the display part 103 is detached from the main body 101 so as to be plated on a table. With the main body 101 held by the subject, the photographing part 105 is rotated by 90 degrees such that the photographing opening 110a faces to the subject side. In the case the photographing part 105 is directed to the upper side (the side for mounting the display part 103 )of the main body 101, since the photo is taken in the upside down direction with respect to the far-vision measurement, it is displayed on the display 103 after correction by the calculation control part 130. With the photographing part 105 used in the direction facing to the bottom surface side of the main body 101, the correction is not needed.

The subject in the near-vision working posture is commanded to adjust the position of the photographing opening 110a at a desired near-vision distance himself. In this case, if a paper piece with characters written on is disposed on the photographing opening 110a, it is easier for the subject to dispose the same at the desired near-vision distance. After positioning, the paper piece is eliminated so that the subject can be gazed at the photographing opening 110a. Accordingly, the camera 110 can be provided at the gazing distance of the subject. Moreover, it is also possible to apply a mark to be the gazing target at the center of the photographing opening 110a.

When the near-vision position is determined accordingly, the inspector rotates the photographing part 105 so that the photo can be taken from the sight direction (visual line direction). The adjustment can be executed by driving the photographing part 105 such that the right and left subject's eye images on the display 103a can be disposed at the center. Moreover, the photographing direction can be aligned with the sight direction (visual line direction) also by driving the photographing part 105 by the subject himself such that his own eyes viewed from himself are shown on the mirror 106. Since the near-vision distance adjusted by the subject is detected by the distance sensors 116 so as to be displayed on the display 103a, the near-vision distance desired by the subject can be observed.

After positioning of the photographing part 105, the switch 107 is pressed (or the measurement item 146 is selected) for photographing the subject's eye images so as to be stored in the memory 131. At the same time, the sight angle (visual line angle) with respect to the horizontal direction is detected by the tilt sensor 115 so as to be stored in the memory 132 as well as the sight angle (visual line angle) is displayed on the display 103a.

FIG. 14B is a diagram for explaining the method for finding the near-vision eye points and the PD. The two reference point images 124' on the scale plate image 122' are designated, respectively. Similar to the case of the far-vision measurement, the calculation control part 130 calculates the correction ratio of the photography magnification and the tilt angle in the right and left direction.

In the near-vision measurement wherein the subject's eye images are photographed from the sight direction (visual line direction), the vertical width of the frame image F' is photographed with a flat shape with respect to the frame image in the far-vision measurement according to the downward sway of the subject's eyes. Therefore, in order to measure the eye points in the upper and lower direction, the flatness is corrected as follows. The calculation control part 130 takes the positions of the reference point images 124' designated in the near-vision screen and the positions of the two reference point images 124' found in the far-vision measurement corresponding with each other. Then, based on the corresponding position data, the vertical lines $180_R$, $180_L$ are displayed such that the straight line linking the intersections 170, 171 and the straight line linking the intersections 173, 174 shown in FIG. 14A are positioned on the frame image F' of FIG. 14B by image process. The inspector designates the intersections 170', 171', 173' and 174' of the vertical lines $180_R$, $180_L$ and the inner side of the frame F by the cursor mark 140 (only either one of the vertical lines can also be designated). The calculation control part 130 calculates the ratio for correcting the flatness of the vertical width from the distance between the intersections 170', 171' and the intersections 170, 171 obtained in the far-vision measurement.

Similar to the case of the far-vision measurement, the near-vision PD is calculated by designating the right and left pupillary centers $_NC_R$, $_NC_L$, respectively by moving the cursor mark 140. Moreover, the position data of the near-vision eye points can be provided as follows.

Figure 19:
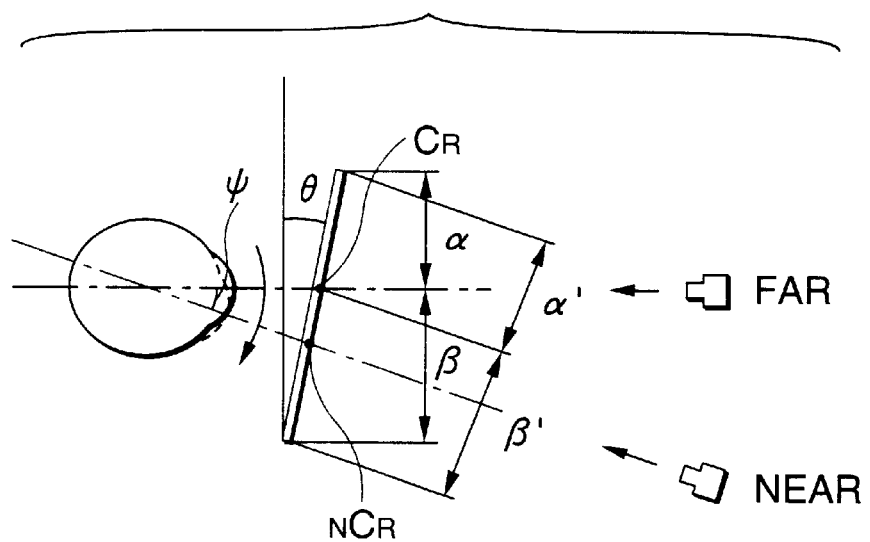
FIG. 19 is a diagram showing the method for finding the downward swaying angle.

As mentioned above, by designating the intersections 170', 171', 173' and 174', the positional relationship of the pupillary centers $_NC_R$, $_NC_L$ with respect to these points can be found out. That is, the positional relationship (direction and distance) of the right eye pupillary center $_NC_R$ with respect to the vertical line $180_R$ in the right and left direction and the positional relationship (direction and distance) with respect to the intersections 170' and 171' in the upper and lower direction can be obtained. Similarly, the positional relationship of the left eye pupillary center $_NC_L$ can also be obtained. As to the positional relationship in the upper and lower direction, the actual distance can be obtained by the correction of the flatness in the vertical width and the correction of the forward tilting angle as mentioned above (see FIG. 19). Accordingly, the position data of the near-vision eye points can be calculated from the far-vision pupillary center $C_R$, $C_L$. Since the inward amount with respect to the far-vision eye point can be learned from the position data, the near-vision single eye PD can be provided by subtracting the inward amount from the far-vision single eye PD.

Figure 20:
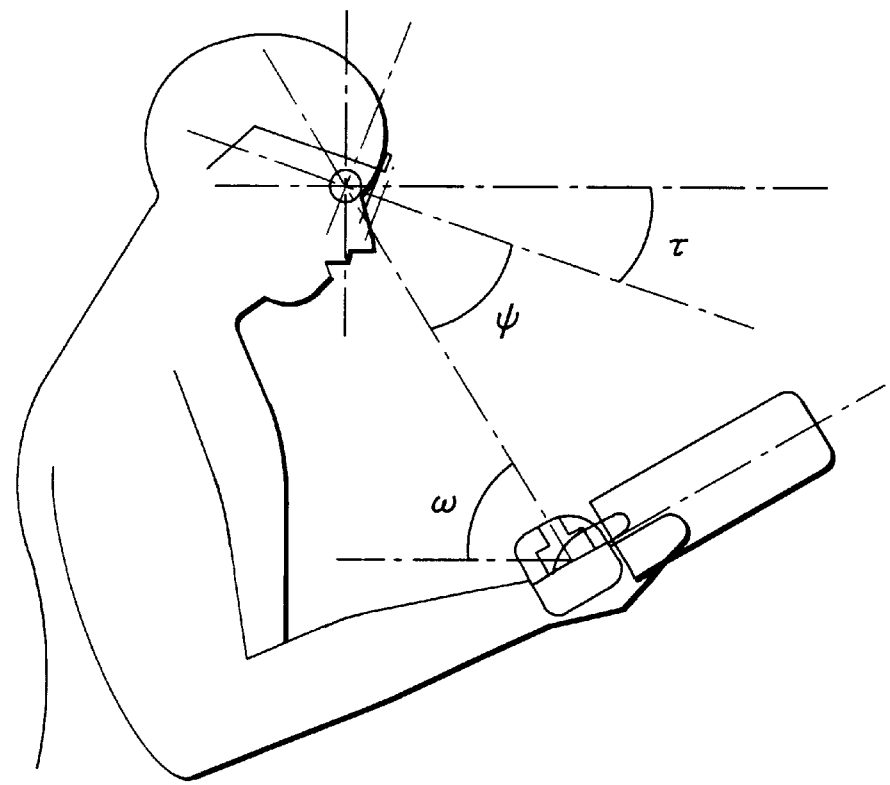
FIG. 20 is a diagram showing the method for finding the tilt angle of the subject face.

Further, the downward swaying angle (the angle $\psi$ in FIG. 19) of the subject's eyes can be calculated from the flatness ratio in the vertical width of the frame. Moreover, according to the downward swaying angle $\psi$ and the sight angle (visual line angle) detected by the tilt sensor 115 (the angle $\omega$ in FIG. 20), the tilt angle of the subject's face in gazing at a short distance (the angle $\tau$ in FIG. 20) can be calculated. The downward swaying angle $\psi$ and the tilt angle of the subject's face $\tau$ can be utilized, for example, in design of progressive multi-focus lenses produced by lens manufacturers.

As heretofore mentioned, also in the near-vision eye point measurement, since the photo is taken from the sight direction (visual line direction) with the camera disposed at the gazing target position, compared with the case of photographing with a fixed camera, particularly accurate measurement results can be obtained. Moreover, since the far-vision eye points and the near-vision eye points can be measured accurately according to the environment in use of the subject, the optimum progressive multi-focus lens can be selected.

The optimum progressive multi-focus lens can be selected by preliminarily storing the data of lenses from various manufacturers (such as the positional relationship of the far-vision points and the near-vision points with respect to the lenses and the lens diameter) in the memory 132, and successively displaying the lens images stored in the memory 131 on the display 103a after determination of the PD and the eye points in the far-vision and near-vision measurement. At the time, the lens image is displayed after image process so as to have the same flatness ratio with respect to the frame image F' in the near-vision measurement shown in FIG. 14B, with the far-vision point of the lens image superimposed on the far-vision pupillary center $C_R$ ($C_L$) on the frame image F' (in the state that the lens disposed in the frame is observed). In this state, by observation of the positional relationship between the near-vision pupillary center $_NC_R$ ($_NC_L$) and the near-vision point of the lens image, the optimum lens can be selected. Moreover, by comparison of the lens diameter with the frame image F', insufficiency of the lens diameter can also be confirmed. It is also possible to select the optimum lens automatically by the calculation control part 130 from the lens data and the measurement data, and then display the same on the display 103 for confirmation.

Moreover, it is also conceivable to show on the display 103a the frame image F' after angle correction by image process so as to be the image without the flatness instead of the image process of the lens image for comparison with the lens image and observation.

The obtained measurement data can be transmitted to a frame selector or a lens edger through a communication cable (not illustrated) so as to be utilized for the frame selection or the lens processing data.

Although the eye position was measured with the spectacular frame on in the above-mentioned embodiment, it is needless to say that the PD measurement in the state without wearing the spectacular frame can also be used. In this case, the scale auxiliary tool 120 can be mounted on the head part of the subject.

Moreover, the eye points can also be found by a method by automatic image process of the luminescent information of the photographed spectacular frame image and front eye part instead of the above-mentioned method.

Furthermore, it is also possible to have the subject wear the produced spectacles for confirming the finish state of the spectacles with the device of this embodiment. That is, with the gazing target distance of the device set at the same distance as in the measurement, the subject's eyes gaze at the gazing target by illumination by the lamp 111 via the measuring window 102. Since the reflection luminescent spots are formed on the subject's eyes and the lenses of the spectacular frame by the light flux emitted from the gazing target, if the optical center of the spectacular lenses is disposed appropriately with respect to the sight (visual line) can be confirmed by observation of whether or not both luminescent spots photographed by the camera 110 and shown on the display 103a are concentric.

Figure 16:
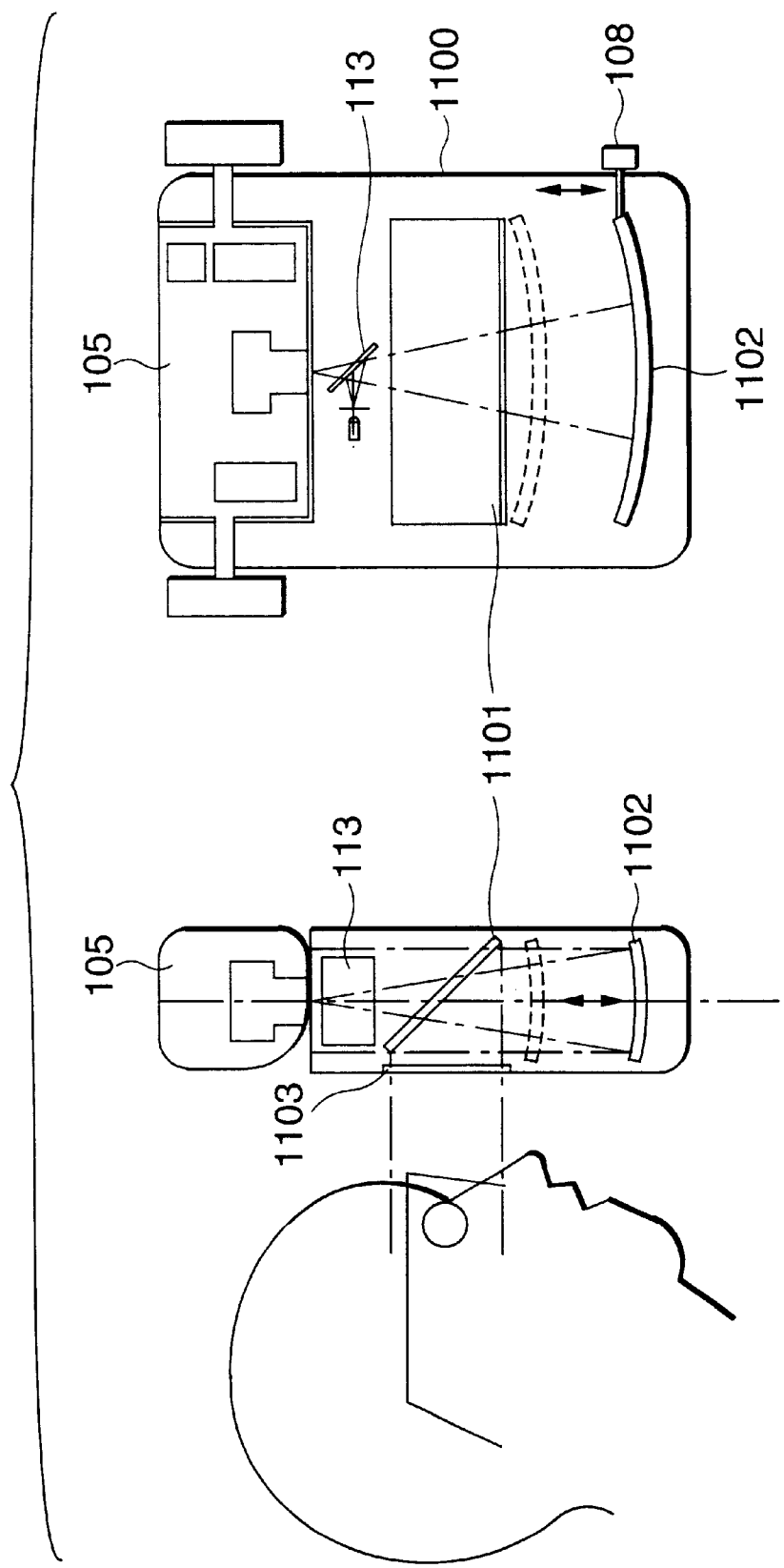
FIG. 16 is a diagram showing an example of an optical system with the showing distance of a gazing target and the photographing distance variable.

Furthermore, as an optical system with the presenting distance of the gazing target and the photographing distance optically variable, a configuration wherein a half mirror 1101 and a movable concave mirror 1102 arranged in the housing of a main body 110 so that the distances can be varied according to movement of the concave mirror 110 as shown in FIG. 16 can be adopted. The subject gazes at the chart (index) with the distance variable through an observation window 1103. In FIG. 16, the element same as the configuration of FIG. 9 are applied with the same numerals and explanation thereof is not given.

As heretofore explained according to the invention, the positions of the subject's eyes for the near-vision to the far-vision according to the environment in use of the spectacles can be measured accurately. Therefore, an appropriate spectacular adjustment can be enabled.

Moreover, since the device for photographing the subject's eyes gazing at a short distance to a long distance and measuring the eye positions is provided with a compact configuration so as to be a handy type, the space for the installation can be saved as well as device with the excellent handling convenience can be realized.

What is claimed is:

1. A device for spectacles for measuring eye points of a subject, comprising:

presenting means for presenting an index to at least one of an inspector and the subject, the presenting means comprising:

a transmission type display disposed adjacent to a spectacular frame of a spectacles worn by the subject; and a display control unit for showing on the display a graphic pattern for measuring an eye point each corresponding to the left eye and the right eye as the index, with the graphic pattern provided such that the subject can judge whether or not a positional relationship between the graphic pattern and a sight of the subject directed to a chart is appropriate;

varying means for varying a positional relationship between an eye of the subject and the graphic pattern as the index, the varying means comprising:

a moving unit for moving the graphic pattern so as to dispose the graphic pattern and the subject's sight with a predetermined positional relationship; and measuring means for measuring the eye points of the subject, the measuring means comprising:

a detecting unit for detecting a moving amount by the moving unit; and a determining unit for determining the eye point of the subject based on the detected moving amount.

2. The device for spectacles according to claim 1, further comprising a mounting unit for mounting the display on the spectacular frame front surface of the spectacles worn by the subject.

3. The device for spectacles according to claim 1, wherein the graphic pattern comprises a small spot-like light transmission region, with the light transmission region provided with a larger light transmission amount compared with a peripheral region thereof.

4. The device for spectacles according to claim 1, wherein the moving unit comprises a member operable by at least one of the inspector and the subject, and the device for spectacles further comprising a voice guide unit for generating a voice guide for guiding the operation by at least one of the inspector and the subject in measuring the eye point.

5. The device for spectacles according to claim 1, wherein the display control unit further shows on the display a second graphic pattern for measuring a position of an inner periphery of the spectacular frame.

6. The device for spectacles according to claim 5, wherein the second graphic pattern comprises a longitudinal line and a lateral line.

7. A device for spectacles for measuring eye points of a subject, comprising:

presenting means for presenting an index to at least one of an inspector and the subject, the presenting means comprising:

a transmission type display disposed adjacent to a spectacular frame of a spectacles worn by the subject;

a first display control unit for showing on the display a graphic pattern for measuring an eye point each corresponding to the left eye and the right eye as the index, a memory for storing a distribution pattern of at least one of a far-vision region, a progressive region, and a near-vision region in a progressive lens; and a second display control unit for displaying the distribution pattern on the display;

varying means for varying a positional relationship between an eye of the subject and the graphic pattern as the index, the varying means comprising:

a moving unit for moving the graphic pattern so as to dispose the graphic pattern and the subject's sight with a predetermined positional relationship; and measuring means for measuring the eye points of the subject, the measuring means comprises:

a detecting unit for detecting a moving amount by the moving unit; and a determining unit for determining the eye point of the subject based on the detected moving amount.

8. The device for spectacles according to claim 7, wherein the second display control unit determines a display position of the distribution pattern based on at least one of the detection result by the detecting unit and the determination result by the determining unit.

9. The device for spectacles according to claim 7, wherein the memory stores a plurality of distribution patterns, and the device for spectacles further comprising a selecting unit for selecting one from the stored plurality of the distribution patterns.

10. A device for spectacles for measuring eye points of a subject, comprising:

presenting means for presenting an index to the subject, the presenting means comprising:

a gazing target presenting optical system comprising a gazing target to be gazed at by subject's eyes as the index, photographing means for photographing a front eye part including both eyes of the subject, the photographing means comprising:

a photographing optical system comprising a photographing unit;

varying means for varying a positional relationship between the subject's eye and the gazing target as the index, the varying means comprising:

a moving unit for varying a presenting distance of the gazing target optically, and further varying a photographing distance by the photographing unit optically for photographing from the substantially same position with respect to the gazing target; and measuring means for measuring the eye points of the subject, the measuring means comprising:

a determining unit for determining the eye points of the subject based on an image photographed by the photographing unit.

11. The device for spectacles according to claim 10, wherein the photographing optical system comprises the same optical path with the gazing target presenting optical system, and an optical member on the common optical path, the moving unit moves the optical member for varying the presenting distance of the gazing target and the photographing distance by the photographing unit optically.

12. The device for spectacles according to claim 10, wherein the photographing unit can be detached from the photographing optical system so as to be disposed at a gazing position with a near-vision distance desired by the subject for photographing the front eye part of the subject.

13. The device for spectacles according to claim 10, further comprising:

a distance detecting unit for detecting a distance between the subject and at least one of the gazing target and the photographing unit optically, and an advising unit for advising the detected distance information, wherein the presenting distance of the gazing target can be varied by the moving unit to the targeted distance of use of the spectacles desired by the subject based on the advised distance information.

14. The device for spectacles according to claim 10, wherein the determining unit determines at least one of an inter-pupillary center distance of the both eyes and the eye points with respect to a spectacular frame of a spectacles worn by the subject.

15. The device for spectacles according to claim 10, further comprising a tilt angle detecting unit for detecting a tilt angle of the photographing unit in a photographing direction with respect to a horizontal direction.

16. The device for spectacles according to claim 10, wherein the gazing target presenting optical system and the photographing optical system are accommodated in a handy type housing.

17. The device for spectacles according to claim 10, further comprising a distance detecting unit for detecting the distance between the subject and at least one of the gazing target and the photographing unit optically, wherein the determining unit determines the eye points of the subject based on the image photographed by the photographing unit and the detected distance.

18. A device for spectacles for measuring eye points of a subject, comprising:
- a gazing target presenting optical system comprising a gazing target to be gazed at by subject's eyes, a presenting distance of the gazing target being variable optically;
- a photographing optical system comprising a photographing unit for photographing a front eye part including both eyes of the subject, a photographing distance by the photographing unit being variable optically for photographing from the substantially same position with respect to the gazing target; and
- a measuring unit for measuring the eye points of the subject based on an image photographed by the photographing unit.

19. The device for spectacles according to claim 18, further comprising:
- a display unit for displaying the photographed image on a screen; and
- a designating unit for designating a desired point on the screen of the display unit,
- wherein the measuring unit measures the eye points based on the designation by the designating unit.

20. The device for spectacles according to claim 18, further comprising:
- a display unit for displaying the photographed image on a screen;
- a memory for storing a distribution pattern of at least one of a far-vision region, a progressive region, and a near-vision region in a progressive lens; and
- a display control unit for displaying the distribution pattern on the screen of the display unit.

21. The device for spectacles according to claim 20, wherein the display control unit determines a display position of the distribution pattern based on the measurement result by the measuring unit.

22. The device for spectacles according to claim 18, wherein the memory stores a plurality of distribution patterns, and
- the device for spectacles further comprising a selecting unit for selecting one from the stored plurality of the distribution patterns.

* * * * *